(12) United States Patent
Sarro Baro et al.

(10) Patent No.: US 10,729,140 B2
(45) Date of Patent: Aug. 4, 2020

(54) BACTERIA WITH NEMATICIDAL ACTIVITY AND THE ABILITY TO PROMOTE PLANT GROWTH

(71) Applicant: FUTURECO BIOSCIENCE, S.A., Olèrdola-Barcelona (ES)

(72) Inventors: Ángela Sarro Baro, Olèrdola-Barcelona (ES); Jose Manuel Lara Sánchez, Olèrdola-Barcelona (ES); Carolina Fernández Castillo, Olèrdola-Barcelona (ES); Marta Almazán García, Olèrdola-Barcelona (ES); Noelia Salgueiro Fernández, Olèrdola-Barcelona (ES)

(73) Assignee: FUTURECO BIOSCIENCE, S.A., Olerdola-Barcelona (ES)

( * ) Notice: Subject to any disclaimer, the term of this patent is extended or adjusted under 35 U.S.C. 154(b) by 354 days.

(21) Appl. No.: 15/519,992

(22) PCT Filed: Oct. 22, 2015

(86) PCT No.: PCT/EP2015/074539
§ 371 (c)(1),
(2) Date: Apr. 18, 2017

(87) PCT Pub. No.: WO2016/062829
PCT Pub. Date: Apr. 28, 2016

(65) Prior Publication Data
US 2017/0367348 A1    Dec. 28, 2017

(30) Foreign Application Priority Data
Oct. 23, 2014 (EP) .................................. 14382416

(51) Int. Cl.
| | | |
|---|---|---|
| *A01N 63/00* | (2020.01) | |
| *A01N 63/10* | (2020.01) | |
| *C12R 1/01* | (2006.01) | |
| *C12N 1/20* | (2006.01) | |
| *C12N 15/82* | (2006.01) | |
| *A01N 25/00* | (2006.01) | |

(52) U.S. Cl.
CPC ............. *A01N 63/10* (2020.01); *A01N 63/00* (2013.01); *C12N 1/20* (2013.01); *C12N 15/8285* (2013.01); *C12R 1/01* (2013.01); *A01N 25/00* (2013.01)

(58) Field of Classification Search
CPC ........ A01N 63/00; A01N 51/00; A01N 53/00; A01N 25/00; A01N 65/00; A01N 41/00; A01N 61/00; A01N 55/00; A01N 59/00; A01N 27/00; C05F 11/08; C05G 3/60; C05G 3/80; C05G 5/40
See application file for complete search history.

(56) References Cited

U.S. PATENT DOCUMENTS

| | | |
|---|---|---|
| 7,592,509 B2 | 9/2009 | Dzhavakhia et al. |
| 8,658,565 B2 | 2/2014 | Thomas et al. |
| 9,433,214 B2 | 9/2016 | Hellwege et al. |
| 2007/0218046 A1 | 9/2007 | Vaaje-Kolstad et al. |
| 2015/0011389 A1 | 1/2015 | Hellwege |
| 2015/0216163 A1 | 8/2015 | Hellwege et al. |

FOREIGN PATENT DOCUMENTS

| | | |
|---|---|---|
| CN | 101177671 A | 5/2008 |
| CN | 102943061 A | 2/2013 |
| EP | 171381 A2 | 2/1986 |
| WO | 0100850 A1 | 1/2001 |
| WO | 2005061533 A1 | 7/2005 |
| WO | 2011128297 A2 | 10/2011 |
| WO | 2012037352 A2 | 3/2012 |
| WO | 2013014227 A1 | 1/2013 |
| WO | 2013110591 A1 | 8/2013 |
| WO | 2013110594 A1 | 8/2013 |
| WO | 2014029747 A1 | 2/2014 |

OTHER PUBLICATIONS

Chen et al. Influence of Lysobacter enzymogenes Strain C3 on Nematodes. Journal of Nematology. 2006;38(2):233-239.*
Vovlas et al. Pathogenicity of the root-knot nematode Meloidogyne javanica on potato. Plant Pathology. 2005;54:657-664.*
Altschul, S., et al.; "Basic Local Alignment Search Tool," J. Mol. Biol., 1990 vol. 215, pp. 403-410.
Chen et al.,; "Influence of Lysobacter enzymogenes Strain C3 on Nematodes," Journal of Nematology, 2006, vol. 38 (2), pp. 233-239.
Yuen G. Y. et al.; "Ecology and biological control of plant pathogens by Lysobacter enzymogenes." Annual meeting of the American-Phytophathological-Society joint with the Canadian-phytopathological-S; Quebec City, Canada. Phytopathology, 2006, vol. 96: S156.
Yuen G. Y. et al., "Effects of lysobacter enzymogenes C3 and its antibiotic dihydromalthophilin on nematodes," Annual meeting of the American-Phytopatological-Society joint with the Canadian-Phytophatological-S; Quebec City, Canada. Phytopathology, 2006, 96: S128.
Yin H. et al., "Culture and non-culture based methods to detect Lysobacter enzymogenes in soil," Annual Meeting of the American-Phythopathology-Society; Portland, USA. 2009; www.apsnet.org/meetings/Documents/2009_Meeting_Abstracts/a09ma877.htm.
Hayward, A.C. et al.; "Stenotrophomonas and Lysobacter: ubiquitous plant-associated gamma-proteobacteria of developing significance in applied microbiology," 2010, Journal of Applied Microbiology, vol. 108(3), pp. 756-770.

(Continued)

*Primary Examiner* — Lynn Y Fan
(74) *Attorney, Agent, or Firm* — Tristan A. Fuierer; Olive Law Group, PLLC

(57) ABSTRACT

The invention relates to a microorganism from the species *Lysobacter enzymogenes*, having nematicidal activity and the ability to promote plant growth. The invention also provides methods for obtaining a biomass of said microorganism, as well as methods for biologically controlling nematodes, for treating and preventing plant infection caused by nematodes, and for promoting plant growth based on the use of said microorganism or of phytosanitary products obtained therefrom.

12 Claims, 20 Drawing Sheets
Specification includes a Sequence Listing.

(56) References Cited

OTHER PUBLICATIONS

Hoseong et al.,; Insight Into Genes Involved in the Production of Extracellular Chitinase in a Biocontrol Bacterium Lysobacter enzymogenes C-3, Plant Pathology Journal, 2012, vol. 28(4), pp. 439-445.
Lee, et al.,; "Biocontrol potential of Lysobacter antibioticus HS124 against the root-knot nematode, Meloidogyne incognita, causing disease in tomato," Nematology 2013, vol. 15(5), pp. 545-555.
Lee, et al.; "Nematicidal activity of Lysobacter capsici YS1215 and the role of gelatinolytic proteins against root-knot nematode," biocontrol science and technology, 2013, vol. 23(12), pp. 1427-1441.
Park, et al.; "Sampling Selection Factors that Enhance the Diversity of Microbial Collections: Application to Biopesticide Development," Plant Pathology Journal, 2013, vol. 29(2), pp. 144-153.
Stokes C. E. et al., "Diversity of fungal and bacterial communities in tip/end rot disease sweetpotatoes," Meeting of the American-Phytopathological_Society (APS) Southern-Division; Baton Rouge, USA. Phytopathology 2013, 103(Suppl. 1):S1.10.
Lee Yong Seong et al., "Purification and properties of a Meloidogyne-antagonistic chitinase from Lysobacter capsici YS1215," Nematology 2014, vol. 16(1), pp. 63-72.
Ya Li, University of Nebraska Lincoln Digital Commons@University of Nebraska Lincoln Theses, Dissertations, and Student Research in Agronomy and Horticulture Agronomy and Horticulture Department Phenotypic Diversity in Lysobacter enzymogenes in Relations to Biological Control, 2014.
Christensen, P.; "*Lysobacter*, a New Genus of Nonfruiting, Gliding Bacteria with a High Base Ratio," International Journal of Systematic Bacteriology 1978, vol. 28(3), pp. 367-393.
Yin H.et al., Isolation and comparison of new Lysobacter enzymogenes strains for biological control traits. 100th Annual Meeting of the American-Phytopathological-Society, Minneapolis, USA. 2008.
Toyota, et al.; "Recent Trands in Microbial Inoculants in Agriculture," Microbes and Environments, 2013, vol. 28(4), pp. 403-404.
International Search Report, dated Dec. 4, 2015.

* cited by examiner

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: Synthetic Construct

<400> SEQUENCE: 1
agtttgatcc tggctcag                                                    18

<210> SEQ ID NO 2
<211> LENGTH: 21
```

<212> TYPE: DNA
<213> ORGANISM: Artificial Sequence
<220> FEATURE:
<223> OTHER INFORMATION: Synthetic Construct

<400> SEQUENCE: 2
acggttacct tgttacgact t                                            21

<210> SEQ ID NO 3
<211> LENGTH: 946
<212> TYPE: DNA
<213> ORGANISM: Lysobacter enzymogenes
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (848)..(848)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (866)..(866)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (944)..(944)
<223> OTHER INFORMATION: n is a, c, g, or t

<400> SEQUENCE: 3
cggcagcaca gnggagcttg ctccttgggt ggcgagtggc ggacgggtga ggaatacgtc    60
ggaatctgcc tatttgtggg ggataacgta gggaaactta cgctaatacc gcatacgacc   120
tacgggtgaa agtgggggac cgcaaggcct cacgcagata gatgagccga cgtcggatta   180
gctagttggc ggggtaaagg cccaccaagg cgacgatccg tagctggtct gagaggatga   240
tcagccacac tggaactgag acacggtcca gactcctacg ggaggcagca gtggggaata   300
ttggacaatg ggcgcaagcc tgatccagcc atgccgcgtg tgtgaagaag gccttcgggt   360
tgtaaagcac ttttgtccgg aaagaaaagc ttagggttaa taaccttgag tcatgacggt   420
accggaagaa taagcaccgg ctaacttcgt gccagcagcc gcggtaatac gaagggtgca   480
agcgttactc ggaattactg ggcgtaaagc gtgcgtaggt ggtttgttaa gtctgatgtg   540
aaagccctgg gctcaacctg gaatggcatt ggaaactggc ttactagagt gcggtagag   600 ggtagcggaa ttcccggtgt agcagtgaaa tgcgtagata tcggaggaac atctgtggc   660 gaaggcggct acctggacca gcactgacac tgaggcacga aagcgtgggg agcaaacagg   720
attagatacc ctggtagtcc acgccctaaa cgatgcgaac tggatgttgg gggcaacttg   780

-continued

```
gccctcagta tcgaagctaa cgcgttaagt tcgccgccng ggaagtacgg tcgcaagact    840
gaaactcnng gaattgacgg gggccngcac aagcggtgga gtatgtggtt taattcnatg    900
cancgcgaag aaccttacct ggccttgacn tgtcgagaac tttnca                  946
```

BACTERIA WITH NEMATICIDAL ACTIVITY AND THE ABILITY TO PROMOTE PLANT GROWTH

CROSS-REFERENCE TO RELATED APPLICATIONS

This application is filed under the provisions of 35 U.S.C. § 371 and claims the priority of International Patent Application No. PCT/EP2015/074539 filed on 22 Oct. 2015 entitled "BACTERIA WITH NEMATICIDAL ACTIVITY AND ABILITY TO PROMOTE PLANT GROWTH" in the name of Angela SARRO BARO, et al., which claims priority to European Patent Application No. 14382416.7, filed on 23 Oct. 2014, both of which are hereby incorporated by reference herein in their entirety.

FIELD OF THE INVENTION

The present invention is comprised in the field of biological control of nematodes that are able to infect plants. Specifically, the invention relates to bacteria from the species *Lysobacter enzymogenes* with nematicidal activity and/or the ability to promote plant growth, as well as to the use of said bacteria in methods for biologically controlling nematodes.

BACKGROUND OF THE INVENTION

Phytoparasitic nematodes are naturally pathogens, but their interactions with other agents causing diseases make it difficult to measure their real impact on crop yield and to make a large-scale estimate. Phytoparasitic nematodes generally cause yearly losses of between 11 and 14% in economically important crops such as legume, cereal, banana tree, yucca, coconut tree, sugar beet, sugar cane, potato, vegetable, ornamental and fruit crops.

The nematode feeding process can cause a reaction in affected plant cells, resulting in root tip and terminal bud death or weakening, lesion formation and torn tissues, bulges and galls, and stem and leaf wrinkling and deformation. Some of these manifestations are caused by decomposition of the tissue affected by nematode enzymes, which, with or without the aid of toxic metabolites, causes tissue disintegration and cell death. Other symptoms, such as galling caused by nematodes from the genus *Meloidogyne*, are caused by abnormal cell elongation (hypertrophy), by cell division suppression or by controlled cell division process stimulation resulting in the formation of galls (hyperplasia) or of a large number of lateral roots in or close to infection sites.

In some cases, however, symptoms are brought about by biochemical interactions of the plants with the nematodes, affecting general plant physiology, as well as the role nematodes play in forming wounds through which other pathogens, which are primarily responsible for the damage caused, penetrate said plants.

With the application of the new European Directive for the sustainable use of phytosanitary products, most of the chemicals intended for controlling these plant parasites and pathogens are being withdrawn due to their high toxicity and treatment aggressiveness.

An ecological alternative for treating and controlling phytopathogenic nematodes consists of biologically controlling such nematodes by means of the use of microorganisms with nematicidal activity. In this sense, the use of some bacteria strains belonging to the genera *Lysobacter* or *Stenotrophomonas* with nematicidal activity has been described. By way of illustration, various assays have shown that *L. enzymogenes* strain C3 has nematicidal activity against juvenile and adult forms of various phytopathogenic nematodes and that it causes abnormalities in nematode eggs in culture medium (Chen et al., "Influence of *Lysobacter enzymogenes* Strain C3 on nematodes", Journal of Nematology, 38(2):233-239, 2006); specifically, Chen et al., analyzed the influence of *L. enzymogenes* strain C3 on phytopathogenic nematodes *Heterodera schachtii*, *Meloidogyne javanica*, *Pratylenchus penetrans* and *Aphelenchoides fragariae*, and observed that (i) *H. schachtii* egg hatching was 50% in the presence of *L. enzymogenes* strain C3 in agar; (ii) juvenile forms of *M. javanica* died 4 days after exposure to a culture broth with *L. enzymogenes* strain C3 chitin; (iii) immersion of juvenile and adult forms of *A. fragariae*, *M. javanica* and *P. penetrans* in a culture broth of *L. enzymogenes* strain C3 led to rapid death and disintegration of such nematodes; and (iv) exposure of juvenile forms of *H. schachtii* to an *L. enzymogenes* strain C3 culture broth resulted in their rapid immobilization and lysis after 3 days. Nevertheless, Chen et al. do not mention anything about the ability of *L. enzymogenes* strain C3 to promote plant growth.

Chinese patent application CN 101177671 describes *L. enzymogenes* strain OH11 and its use in treating plant diseases; although the possibility of using said strain in treating diseases caused by phytopathogenic nematodes is mentioned, nematicidal activity of said strain is not demonstrated.

Ya Li ("University of Nebraska—Lincoln Digital Commons@University of Nebraska—Lincoln Theses, Dissertations, and Student Research in Agronomy and Horticulture Agronomy and Horticulture Department Phenotypic Diversity in *Lysobacter enzymogenes* in Relations to Biological Control, 2014) discloses the control of plant pathogens by several types of *Lysobacter*, and in particular by several strains of *L. enzymogenes*. This document also discusses the ability of *L. enzymogenes* to promote plant growth, although mentions that no information is available on the ability of *L. enzymogenes* to stimulate plant growth through mechanisms not related to biologic control of plant pathogens.

Therefore, there is a need for new ecological alternatives for biologically controlling phytopathogenic nematodes.

SUMMARY OF THE INVENTION

In a first aspect, the invention relates to a microorganism from the species *Lysobacter enzymogenes*, identified as *L. enzymogenes* strain MR B25, deposited in the Spanish Type Culture Collection (CECT—Colección Española de Cultivos Tipo) with accession number CECT 8565, having nematicidal activity and/or the ability to promote plant growth, or a mutant of said microorganism maintaining said nematicidal activity and/or said ability to promote plant growth.

In a second aspect, the invention relates to a biologically pure culture of a microorganism according to the first aspect.

In a third aspect, the invention relates to a method for obtaining a biomass of the microorganism according to the first aspect comprising culturing said microorganism under conditions suitable for growth.

In a fourth aspect, the invention relates to a biomass of the microorganism according to the first aspect obtainable by means of the method of the third aspect.

In a fifth aspect, the invention relates to a phytosanitary product comprising a microorganism according to the first aspect, a biologically pure culture according to the second aspect or a biomass according to the fourth aspect, and an agriculturally acceptable excipient.

In a sixth aspect, the invention relates to a supplemented seed comprising a seed, and furthermore a microorganism according to the first aspect, or a biologically pure culture according to the second aspect, or a biomass according to the fourth aspect, or a phytosanitary product according to the fifth aspect.

In a seventh aspect, the invention relates to a method for biologically controlling a nematode comprising applying to said nematode a microorganism according to the first aspect, a biologically pure culture according to the second aspect, a biomass according to the fourth aspect, or a phytosanitary product according to the fifth aspect.

In an eighth aspect, the invention relates to a method for preventing plant infection caused by a nematode comprising applying an effective amount of a microorganism according to the first aspect, a biologically pure culture according to the second aspect, a biomass according to the fourth aspect, or a phytosanitary product according to the fifth aspect on said plant, on the seed of said plant, in the soil surrounding said plant or on a nematode susceptible of infecting said plant, or alternatively planting a seed of said plant supplemented with a microorganism according to the first aspect, a biologically pure culture according to the second aspect, a biomass according to the fourth aspect, or a phytosanitary product according to the fifth aspect.

In a ninth aspect, the invention relates to a method for treating a plant infected by a nematode comprising applying an effective amount of a microorganism according to the first aspect, a biologically pure culture according to the second aspect, a biomass according to the fourth aspect, or a phytosanitary product according to the fifth aspect on said plant or in the soil surrounding said plant.

In a tenth aspect, the invention relates to a method for stimulating plant growth comprising applying an effective amount of a microorganism according to the first aspect, a biologically pure culture according to the second aspect, a biomass according to the fourth aspect, or a phytosanitary product according to the fifth aspect on said plant, on the seed of said plant or in the soil surrounding said plant, or alternatively planting a seed of said plant supplemented with a microorganism according to the first aspect, a biologically pure culture according to the second aspect, a biomass according to the fourth aspect, or a phytosanitary product according to the fifth aspect.

DETAILED DESCRIPTION OF THE INVENTION

Figure 1:
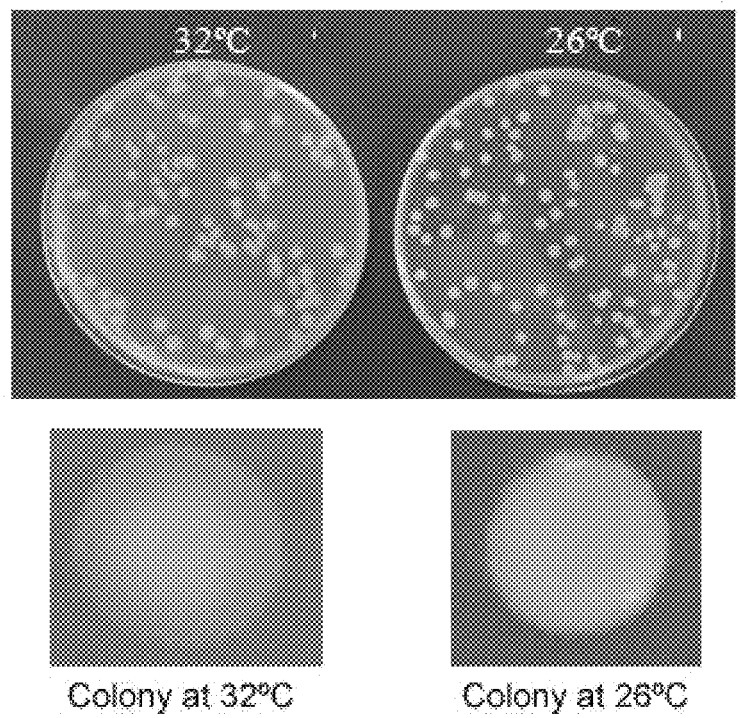
FIG. 1. Morphological characteristics of *L. enzymogenes* strain MR B25 grown at different temperatures in nutritive agar.

The inventors of the present invention have discovered a bacterial strain of species *Lysobacter enzymogenes* (*L. enzymogenes* strain MR B25) with nematicidal and plant growth promoting activity. Specifically, the inventors have observed that said strain is able to inhibit nematode egg hatching from the species *Meloidogyne javanica* in in vitro assays (Example 2) and to induce mortality of *M. javanica* juveniles in vitro (Example 3). Said nematicidal activity was also confirmed in vivo on tomato plants of the "Marmande" variety (Examples 6, 7 and 8). The in vitro nematicidal activity of *L. enzymogenes* strain MR B25 against *M. javanica* eggs and its in vivo activity against *M. javanica* juveniles is surprisingly greater than that of other strains of the same species. The inventors have additionally observed that treating tomato plants with *L. enzymogenes* strain MR B25 unexpectedly promotes the growth of sa id plant (Examples 6, 7 and 9).

The following inventive aspects have been developed based on these discoveries.

Microorganism and Culture

In a first aspect, the invention relates to a microorganism from the species *Lysobacter enzymogenes*, hereinafter microorganism of the invention, identified as *L. enzymogenes* strain MR B25, deposited in the Spanish Type Culture Collection (CECT) with accession number CECT 8565, having nematicidal activity and/or the ability to promote plant growth, or a mutant of said microorganism maintaining said nematicidal activity and/or said ability to promote plant growth.

Said strain was deposited before the date of filing the present patent application in the Spanish Type Culture Collection (CECT), as a legally recognized depositary institution for that purpose in accordance with the Budapest Treaty of Apr. 28, 1977, on international recognition of the deposit of microorganisms for the purposes of patent.

The depositor was Futureco Bioscience, S.A. with registered office at Avenida del Cadi, nave 19-23, Poligono Industrial Sant Pere Molanta, 08799, Olèrdola, Barcelona, Spain.

The morphological and molecular characteristics of said strain are shown in Example 1, and the culture conditions are described below in the context of the method for obtaining biomass of the invention.

The microorganism of the invention belongs to a species identified in the NCBI database by Taxonomy ID: 69. The species *Lysobacter enzymogenes* was described by Christensen and Cook, 1978 (Christensen, P., & Cook, F. D. (1978). *Lysobacter*, a new genus of nonfruiting, gliding bacteria with a high base ratio. *International Journal of Systematic Bacteriology*, 28(3), 367-393).

The term "microorganism of the invention" includes both said microorganism *L. enzymogenes* strain MR B25 (CECT 8565), with nematicidal activity and/or the ability to promote plant growth, and its mutants maintaining said nematicidal activity and/or said ability to promote plant growth.

As it is used herein, the term "mutant" refers to any microorganism resulting from a mutation or change in the DNA of one or several genes of *L. enzymogenes* strain MR B25 (CECT 8565) maintaining essentially the same characteristics as the parent strain [*L. enzymogenes* strain MR B25 (CECT 8565)], and specifically essentially maintaining the nematicidal activity and/or the ability to promote plant growth. The mutant can be produced naturally or intentionally by mutagenesis methods known in the state of the art, such as, for example but not being limited to, growing the original microorganism in the presence of mutagenic or stress-causing agents, or by means of genetic engineering aimed at modifying specific genes.

In a particular embodiment, the mutant of the *L. enzymogenes* strain MR B25 has a genome having a sequence identity of at least 75%, at least 80%, at least 85%, at least 90%, at least 95%, at least 99% or higher with the genome of *L. enzymogenes* strain MR B25. The sequence identity between the genomes of two microorganisms can be determined by using algorithms implemented in a computer and methods which are widely known by the persons skilled in the art. The identity between two nucleotide sequences is preferably determined using the BLASTN algorithm (BLAST Manual, Altschul, S. et al., NCBI NLM NIH Bethesda, Md. 20894, Altschul, S., et al., J., 1990, Mol. Biol. 215:403-410).

In a particular embodiment, the microorganism of the invention has nematicidal activity. In another particular embodiment, the microorganism of the invention has the ability to promote plant growth. In another particular embodiment, the microorganism of the invention has nematicidal activity and the ability to promote plant growth.

As it is used herein, the expression "nematicidal activity" refers to the ability to inhibit egg hatching and/or paralyze larval forms of a nematode in any of their stages or to prevent a nematode from developing or growing.

As it is used herein, the term "nematode" refers to a phylum of pluricellular pseudocoelomate organisms of the group Ecdysozoa. As it is used herein, the term "nematode" includes any nematode. Although the microorganism of the invention can have nematicidal activity on any nematode, it preferably has nematicidal activity on a phytoparasitic or phytopathogenic nematode.

As it is used herein, the term "plant-parasitic nematode" or "plant-pathogenic nematode" or "phytoparasitic nematode" or "phytopathogenic nematode" refers to a nematode with the ability to parasite a plant organism or to cause a disease in a plant organism, including:

Migratory endoparasites: motile nematodes feeding inside plant tissue. All the stages of the life cycle are motile except the egg. They perforate plant tissue, moving from cell to cell. While they feed, they deposit eggs in cortical tissue of the plant or in the soil surrounding the root. Damaged cells release toxins which cause the death of adjacent cells, giving rise to necrotic tissue spots. Pathogenic bacteria and fungi frequently enter through the damaged zones causing rot in the roots. Examples: *Pratylenchus* (*P. vulnus*, *P. penetrans*, *P. brachyurus*, *P. coffeae*, *P. goodeyi*, *P. zeae*, *P. thornei*, *P. neglectus*), *Radopholus* (*R. similis*, *R. citrophilus*), *Scutellonema bradys*, *Hirschmanniella*.

Sedentary endoparasites: the adult penetrates the plant and attaches itself to it, leaving part of its body exposed to the exterior. They generally feed on syncytia. Examples: *Meloidogyne* (*M. incognita*, *M. javanica*, *M. arenaria*, *M. hapla*), *Globodera* (*G. pallida*, *G. rostochiensis*), *Heterodera* (*H. schachtii*, *H. trifolii*, *H. goettingiana*, *H. avenae*).

Ectoparasites: free-living phytophagous nematodes. They only introduce the stylet, which can be very weak (Tylenchus, citrus nematode), in the root affecting only root hairs, or very long (*Longidorus* and *Xiphinema*), allowing them to feed off deep tissue cells. These latter species are very problematic on an agronomical level because they are virus-transmitting nematodes.

The microorganism of the invention can have nematicidal activity on any plant-parasitic or -pathogenic nematode of those mentioned above. Illustrative, non-limiting examples of plant-parasitic or -pathogenic nematodes on which the microorganism of the invention can have nematicidal activity include nematodes belonging to the genera *Meloidogyne*, *Heterodera*, *Globodera*, *Pratylenchus*, *Paratylenchus*, *Rotylenchus*, *Xiphinema*, *Trichodorus*, *Ditylenchus*, *Criconemella*_____ (*Mesocriconema*), *Helicotylechus*, *Longidorus*, *Paratrichodorus*, *Belonolaimus* and *Radopholus*.

In a particular embodiment, the microorganism of the invention has nematicidal activity on a nematode selected from the genera *Meloidogyne*, *Globodera*, *Heterodera*, *Pratylenchus*, *Tylenchulus*, *Radopholus* and *Xiphinema*. In an even more particular embodiment, the microorganism of the invention has nematicidal activity on a nematode from the genus *Meloidogyne*. In a still more particular embodiment, the microorganism of the invention has nematicidal activity on *Meloidogyne javanica*. In another particular embodiment, the microorganism of the invention has nematicidal activity on a nematode from the genus *Globodera*.

As it is used herein, the term "*Meloidogyne*" refers to a genus of nematodes identified in the NCBI database by Taxonomy ID: 189290.

As it is used herein, the term "*Meloidogyne javanica*" or "*M. javanica*" refers to a species of the so-called root-knot nematodes identified in the NCBI database by Taxonomy ID: 6303. Root-knot nematodes are plant-parasitic nematodes from the genus *Meloidogyne* infecting plant roots giving rise to the development of galls in root knots which drain out the plant nutrients.

As it is used herein, the term "*Globodera*" refers to a genus of nematodes identified in the NCBI database by Taxonomy ID: 31242 and also called "cyst-forming nematodes".

A nematode life cycle includes 6 stages, including the egg, 4 juvenile or larval stages and one adult stage. All stages, with the exception of the first juvenile that is formed from the egg, are preceded by a molt.

The microorganism of the invention can have nematicidal activity on any of the stages of a nematode, including eggs, juvenile forms and adult forms. In a particular embodiment, the microorganism of the invention has nematicidal activity on eggs of nematodes. In another particular embodiment, the microorganism of the invention has nematicidal activity on juvenile forms of nematodes. In a particular embodiment, the microorganism of the invention has nematicidal activity on eggs of nematodes and on juvenile forms of nematodes. In another particular embodiment, the microorganism of the invention has nematicidal activity on the adult form of nematodes. In another particular embodiment, the microorganism of the invention has nematicidal activity on eggs of nematodes and on the adult form of nematodes. In another particular embodiment, the microorganism of the invention has nematicidal activity on juvenile forms of nematodes and on the adult form of nematodes. In another particular embodiment, the microorganism of the invention has nematicidal activity on eggs of nematodes, on juvenile forms of nematodes and on the adult form of nematodes.

The nematicidal activity of a microorganism can be determined by the person skilled in the art by means of any in vivo or in vitro assay that allows determining and/or quantifying the ability of a microorganism to interfere with nematode development in any of its stages. Illustrative examples of said assays are the following:

An in vitro assay on eggs in which, after an incubation period of time of the eggs of nematodes under conditions suitable for hatching, the percentage of eggs that hatched in the presence of the control agent, in this case the microorganism whose eventual nematicidal activity is to be known, compared with a control sample (for example, the same amount of eggs of nematodes in the absence of the control agent), is determined. By means of such assay the "nematicidal efficacy" parameter can be determined as the difference in the percentage of eggs that hatched in the presence of the microorganism with respect to the control in a specific time period. Any significant reduction in the percentage of eggs that hatched in the presence of the microorganism with respect to the control indicates that said microorganism has nematicidal activity.

An in vitro assay on juveniles in which, after an incubation period of time of juvenile forms of nematodes under conditions suitable for development, the percentage of live juveniles in the presence of the control agent, in this case the microorganism whose eventual nematicidal activity is to be known, compared with a control sample (for example, the same amount of juveniles in the absence of the control agent), is determined. The "nematicidal efficacy" determined by means of such assay is defined as the percentage of mortality of juveniles corrected with respect to the control in a specific time period. Any significant reduction in the percentage of live juveniles in the presence of the microorganism with respect to the control indicates that said microorganism has nematicidal activity.

A in vivo assay in which a plant is inoculated with juvenile forms of the nematode, and after a time period under conditions suitable for plant growth and after being treated with the microorganism whose eventual nematicidal activity is to be known, the number of eggs, and/or juveniles and/or adults of the nematode present in the plant treated with the microorganism compared with the control (for example, said plant untreated with the microorganism) is evaluated. The "nematicidal efficacy" determined by means of such assay is defined as the difference in the percentage of eggs and/or juvenile and/or adult stages in the presence of the microorganism corrected with respect to the control in a specific time period. Any significant reduction in the percentage of eggs and/or juveniles and/or adults in the presence of the microorganism with respect to the control indicates that said microorganism has nematicidal activity. In a particular embodiment, the nematicidal activity of the microorganism of the invention is determined by means of the assays used in Examples 2-8 of the present specification.

The microorganism of the invention has a nematicidal efficacy of at least 2%; at least 5%; at least 10%; at least 15%; at least 20%; at least 25%; at least 30%; at least 40%; at least 50%; at least 60%; at least 70%; at least 80%; at least 90%; at least 95%; at least 99% or 100% with respect to a control.

In a particular embodiment, the microorganism of the invention has a nematicidal efficacy, measured as efficacy corrected in the reduction of M. javanica egg hatching, determined by means of an in vitro assay on M. javanica eggs using the conditions described in Example 2 of the specification of at least 80% with respect to a control; or of around 60% (59.80%) with respect to the chemical (fenamiphos) used as a reference, using the conditions described in Example 4 of the specification; or of around 30% (30.24%) using the conditions described in Example 5 of the specification.

As it is used herein, the expression "ability to promote plant growth" refers to the ability to facilitate or stimulate development of the plant root system, stem growth, and/or development of the leaf biomass, etc. The plant growth-promoting ability (activity) of the microorganism of the invention (or of any microorganism whose plant growth-promoting ability or activity is to be known) can be determined by the person skilled in the art by means of any assay in which a parameter related to the plant growth, such as height, root dry weight or fresh weight, aerial dry weight or fresh weight, etc., in the presence or absence of the microorganism in question is determined.

In a particular embodiment, the ability to promote plant growth is the ability to increase plant biomass. In the context of the present invention, "plant biomass" is understood as the amount of organic matter present in a plant, i.e., the organic matter forming both the aerial part of the plant, that is, the stem, the stalk, the leaves, the branches, the fruit, inflorescences, etc. (aerial biomass), and the underground part thereof, i.e., roots, bulbs, tubercles, etc. (underground biomass). The "plant biomass" can be measured as "dry weight" or as "fresh weight" of the plant or certain parts of the plant, as appropriate.

As it is used herein, the term "fresh weight" relates to the weight of the plant as a whole or of part of the plant, such as the leaves, stems, flowers and other aerial structures (aerial fresh weight), or the roots (root fresh weight).

As it is used herein, the term "dry weight" refers to the weight of the plant as a whole or of part of the plant, such as the leaves, stems, flowers and other aerial structures (aerial dry weight), or the roots (root dry weight) once all possible water has been removed through a drying process.

In the present invention, the effect on the plant of obtaining a growth rate exceeding 1 is understood as "plant biomass increase in a plant", wherein growth rate (GR) is defined by the formula:

$$GR = \text{Final weight/initial weight.}$$

As a person skilled in the art will understand, there are other parameters in the state of the art that are either directly or indirectly related to GR and can be used for determining plant biomass growth in a plant. Examples of said parameters, without being limiting, include:

relative growth rate (RGR) or gain in biomass per unit of biomass and time, and is defined by the formula:

$$RGR = (LnP_2 - LnP_1)/(t_1 - t_2)$$

wherein $P_1$ and P2 are plant weight at times 2 and 1 ($t_2$–$t_1$, respectively) [Valladares, F. 2004, Ecología del bosque mediterráneo en un mundo cambiante, pp. 191-227. Ministry of the Environment, EGRAF, S.A., Madrid];

leaf area ratio (LAR) or leaf area and total plant weight ratio. It is expressed in $m^2$ (leaf) $kg^{-1}$ (plant). The leaf area can be measured by several methods. There are automatic leaf area measuring devices provided with a video camera, digitalization card and image• analysis software that allow area measurements (in addition to measurements of other dimensions: width, length, etc.) of a number of leaves fairly quickly. Another system is to photocopy or scan leaves and estimate the surface area by means of an image analysis program. Another simple alternative is to cut out the silhouettes of photocopied leaves and weight them, using a cut out of the same paper with a known surface area to calibrate the weight/area ratio. Once the surface area of the leaves is measured, the leaves are kept in paper envelopes with their identification, dried in an incubator and weighed to thus obtain the "dry weight";

specific leaf area (SLA) or leaf area and leaf weight ratio. It is expressed in m2 (leaf) $kg^{-1}$ (leaf);

leaf mean fraction (LMF) or leaf biomass and total plant biomass ratio. It is expressed as kg (leaf) $kg^{-1}$ (plant);

net assimilation rate (NAR) or rate of plant weight increase per unit of leaf area. It is expressed in kg (plant) $m^{-2}$ (leaf) $day^{-1}$. The relative growth rate is equal to the product of LAR and NAR.

Other parameters for analyzing growth include:

stem mass fraction (SMF) or stem biomass and total plant biomass ratio. It is expressed as kg (stem) $kg^{-1}$ (plant);

root mass fraction (RMF) or root biomass and total plant biomass ratio. It is expressed as kg (root) $kg^{-1}$ (plant); and content in dry matter (DM) or plant dry weight and fresh weight ratio. It is expressed in kg (dry weight) $kg^{-1}$ (fresh weight).

Any significant increase in any of the preceding parameters related to plant growth in the presence of a microorganism, for example, a microorganism of the invention, with respect to the control (the same plant in the absence of the microorganism) indicates that said microorganism has the ability to promote plant growth.

In a particular embodiment, the ability of a microorganism, such as a microorganism of the invention, for example, to promote plant growth is determined by means of a parameter selected from plant height, root fresh weight, aerial fresh weight, root dry weight and aerial dry weight following a method such as the one described in Example 9 of the specification.

In a particular embodiment, the microorganism of the invention has the ability to promote plant growth in a plant of a family selected from Solanaceae, Musaceae, Fabaceae, Malvaceae, Amaranthaceae, Vitaceae, Rutaceae, Cucurbitaceae, Poaceae, Rubiaceae, ornamental plant families or a family of fruit trees.

As it is used herein, the term "Solanaceae" refers to a family of plants identified in the NCBI database by Taxonomy ID: 4070. It is a family of herbaceous or woody plants with simple, alternate leaves and without stipules, belonging to the order Solanales, of the dicotyledons. Illustrative, non-limiting examples of plants from the family Solanaceae include the genera *Solanum, Lycianthes, Cestrum, Nolana, Lycium, Nicotiana* and *Brunfelsia*.

In a particular embodiment, the microorganism of the invention has the ability to promote plant growth in a plant from the family Solanaceae, preferably from the genus *Solanum*.

As it is used herein, the term "*Solanum*" refers to a genus of plants identified in the NCBI database by Taxonomy ID: 4107. Illustrative, non-limiting examples of plants from the genus *Solanum* include *S. lycopersicum* (tomato), *S. tuberosum* (potato) and *S. melongena* (eggplant).

In a particular embodiment, the microorganism of the invention has the ability to promote plant growth in a plant from the family Solanaceae, from the genus *Solanum* and from the species *Solanum lycopersicum*.

As it is used herein, the term "*Solanum lycopersicum*" refers to a species of plants identified in the NCBI database by Taxonomy ID: 4081, commonly known as the tomato. The term "*Solanum lycopersicum*" includes any tomato variety, including by way of illustration *S. lycopersicum* var. *cerasiforme* (cherry tomato).

In a particular embodiment, the microorganism of the invention has the ability to promote plant growth in a plant from the species *Solanum lycopersicum* "Marmande" variety. The "Marmande" variety is an extremely early tomato variety. The plant has a high stem and the number of fruits per floral level ranges from 5 to 10; said fruits are large, flattened and ribbed, and have a bright red color.

As it is used herein, the term "Musaceae" refers to a family of plants identified in the NCBI database by Taxonomy ID: 4637. Illustrative, non-limiting examples of plants from the family Musaceae include the genera *Musa* and *Ensete*. In a particular embodiment, the seed belongs to the genus *Musa* (Taxonomy ID: 4640) to which different species producing bananas belong.

As it is used herein, the term "Fabaceae" refers to a family of plants, commonly known as legumes, identified in the NCBI database by Taxonomy ID: 3803. In a particular embodiment, the plant belongs to the genus *Glycine*. In an even more particular embodiment, the plant belongs to the plant species *Glycine max* (Taxonomy ID: 3847) which produces soybean.

As it is used herein, the term "Malvaceae" refers to a family of plants identified in the NCBI database by Taxonomy ID: 3629. In a particular embodiment, the plant belongs to the genus *Gossypium* (Taxonomy ID: 3847), to which different species producing cotton belong.

As it is used herein, the term "Amaranthaceae" refers to a family of plants identified in the NCBI database by Taxonomy ID: 3563. In a particular embodiment, the plant belongs to the genus *Beta*, more specifically to the plant species *Beta vulgaris* (Taxonomy ID: 161934) which produces beet.

As it is used herein, the term "Vitaceae" refers to a family of plants identified in the NCBI database by Taxonomy ID: 3602. In a particular embodiment, the plant belongs to the genus *Vitis*, more specifically to the plant species *Vitis vinifera* (Taxonomy ID: 29760) which produces grapes.

As it is used herein, the term "Rutaceae" refers to a family of plants identified in the NCBI database by Taxonomy ID: 23513. In a particular embodiment, the plant belongs to the genus *Citrus* (Taxonomy ID: 2706) formed by different plants species producing citrus fruits such as oranges, lemons, grapefruits and limes.

As it is used herein, the term "Cucurbitaceae" refers to a family of plants identified in the NCBI database by Taxonomy ID: 3650. Illustrative, non-limiting examples of plants from the family Cucurbitaceae whose seeds can be used to obtain the supplemented seed of the invention include the genera *Cucurbita* (plants producing pumpkin and zucchini), *Lagenaria, Citrullus* (plants producing watermelon), *Cucumis* (plants producing cucumber and melon) and *Luffa*. In a particular embodiment, the plant belongs to the family Cucurbitaceae.

As it is used herein, the term "Poaceae" refers to a family of plants identified in the NCBI database by Taxonomy ID: 4479. Illustrative, non-limiting examples of plants of this family are plants producing wheat, barley, rice or corn.

As it is used herein, the term "Rubiaceae" refers to a family of plants identified in the NCBI database by Taxonomy ID: 24966. In a particular embodiment, the plants from the family Rubiaceae are plants that produce coffee.

As it is used herein, the term "ornamental" refers to plants that are cultured and sold for decorative purposes given their aesthetic characteristics, such as flowers, leaves, aroma, foliage texture, fruits or stems in gardens, an indoor plant or a cut flower. Illustrative, non-limiting examples of families included in this definition are Liliaceae (including species of tulips, dracaenas or lilies), Iridiaceae (including species from the genera *Crocus, Iris* or *Gladiolus*), Amaryllidaceae (including species such as a daffodil), Rosaceae (including species of roses) or Geraniae (including species of geraniums).

As it is used herein, the term "fruit tree" refers to any woody tree or vine that produces a fruit of agricultural or industrial interest. The term "fruit" refers to a part of a plant with flowers that is derived from specific tissues of the flower and is not limited to culinary fruits. Illustrative examples of fruit trees whose seeds can be used to obtain the supplemented seed of the invention include avocado, almond tree, banana tree or plantain tree, cherry tree, plum tree, citrus trees, apricot tree, peach tree, durian tree, orange tree, sour cherry tree, mango, apple tree, quince tree, loquat tree, walnut tree and pear tree.

In a second aspect, the invention relates to a biologically pure culture of the microorganism of the invention.

As it is used herein, the expression "biologically pure culture" refers to a culture in which the microorganism of the invention can be found in a proportion of 95% or higher, for example 96% or higher, 97% or higher, 98% or higher, 99% or higher, or 100%, compared with other organisms present in the culture. As it is used herein, the term "culture" refers to a population of the microorganisms of the invention. A culture can comprise other elements in addition to the microorganisms of the invention, such as the culture medium or any other substance that can be added to the culture medium that is beneficial for culture growth or maintenance. The term "culture medium" or "medium" is recognized in the art and generally refers to any substance or preparation that is used for the culture of live cells. As it is used in reference to a cell culture, the term "medium" includes the components of the environment surrounding the cells. The medium can be solid medium, liquid medium, gaseous medium, or a mixture of the phases and materials. The growth media include liquid culture media as well as liquid media that do not support cell growth. The medium also includes gelatinous media such as agar, agarose, gelatin and collagen matrices. Exemplary gaseous media include the gas phase to which the cells growing in a Petri dish or another solid or semisolid support are exposed. The term "medium" also refers to a material that must be used in a cell culture, even if it has still not been contacted with the cells. In other words, a liquid rich in nutrients prepared for bacterial culture is a medium. Likewise, a powder mixture which when mixed with water or with another liquid becomes suitable for the cell culture can be called a "powder medium". "Defined medium" refers to the media made up of components having a defined chemical constitution (generally purified). The defined media do not contain biological extracts that are not completely characterized, such as meat broth and yeast extract. "Rich medium" includes media designed to support growth of most or all viable forms of a particular species. Enriched media often include complex biological extracts. Any conventional culture medium suitable for *L. enzymogenes* known in the art can be used in the present invention, such as, for example, nutrient broth made up of meat extract (3 g/L) and soy peptone (5 g/L); or TSB medium made up of tryptone (17 g/L), soy peptone (3 g/L), NaCl (5 g/L), $K_2HPO_4$ (2.5 g/L) and glucose (2.5 g/L). In a particular embodiment, the culture medium that can be part of the biologically pure culture of the invention is made up of: yeast extract (5 g/L), tryptone (10 g/L) and sodium chloride (10 g/L).

Biomass and Method for Obtaining Biomass

The microorganism of the invention can be used in the form of a biomass of said microorganism multiplied in culture in methods for biologically controlling nematodes, or for preventing or treating plant infection caused by nematodes, or for promoting plant growth in a plant.

Therefore, in a third aspect the invention relates to a method for obtaining a biomass of the microorganism of the invention, comprising culturing said microorganism under conditions suitable for growth.

As it is used herein, the term "biomass" refers to the biological material of living organisms, particularly of the microorganism of the invention.

Conditions suitable for growth of the microorganism of the invention will be those conditions which allow microorganism maintenance and multiplication. In a particular embodiment, said conditions comprise culturing the microorganism of the invention in the presence of a culture medium or substrate containing one or several carbon sources, one or several nitrogen sources and inorganic and organic salts at concentrations suitable for obtaining maximum biomass yields. Said medium or substrate can be solid or liquid. The carbon sources consist of monosaccharides, polysaccharides, cereals or plant extracts. The nitrogen sources comprise plant protein hydrolysates, peptones or free, pure or mixed amino acids. The salts are sulfates or phosphates of elements such as Na, Ca, Mg, Fe, or K. In a particular embodiment, the culture medium or substrate contains between 1 and 5 carbon sources, between 1 and 5 nitrogen sources and between 1 and 10 salts.

In a particular embodiment, the conditions suitable for growth of the microorganism of the invention comprise culturing the microorganism in the culture medium under constant temperature, pH and oxygenation conditions. In a particular embodiment, the temperature is comprised between 25° C. and 35° C., preferably 30° C. In a particular embodiment, the pH is comprised between 5.0 and 9.0, preferably between 6.0 and 8.0, more preferably 7.0. In a particular embodiment, oxygenation is achieved by means of stirring at speeds between 200 and 500 rpm and/or supplying sterile air at a fixed flow rate between 0.5 and 1.5 vvm; preferably at speeds between 200 and 300 rpm and/or supplying sterile air at a fixed flow rate between 0.8 and 1.2 vvm; more preferably, oxygenation is achieved by means of stirring for 24 hours at a speed of 250 rpm and/or supplying sterile air at a fixed flow rate of 1.0 vvm.

The time during which the microorganism must be kept under conditions suitable for growth is the time needed for the microorganism to reach a concentration corresponding to a minimum substrate to biomass conversion of 80%. In a particular embodiment, said time of growth for reaching these yields is between 1 and 10 days.

Once the microorganism growth step has ended, the obtained biomass can be recovered from the used up substrate by applying one or several unit operations which can comprise centrifugation, decantation, filtration or a combination of several of these operations. Therefore, in a particular embodiment, the method for obtaining the biomass of the microorganism of the invention additionally comprises a step for separating the biomass from the substrate. In an even more particular embodiment, said biomass is separated from the substrate by means of one or more steps of centrifugation, decantation or filtration, or a combination thereof.

In a particular embodiment, after separating the biomass from the substrate the biomass can be dried using low temperature and/or pressure conditions to remove moisture from the biomass. In a more particular embodiment, said conditions are between 18 and 25° C. and between 266.644731 and 799.934192 Pa(2 and 6 mm Hg).

A biomass of the microorganism of the invention is obtained by means of the method of the third aspect. Therefore, in a fourth aspect, the invention relates to a biomass of the microorganism of the invention obtainable by means of the method according to the third aspect.

Phytosanitary Product and Supplemented Seed

In a fifth aspect, the invention relates to a phytosanitary product comprising the microorganism of the invention, the biologically pure culture of the invention or the biomass of the invention, and an agriculturally acceptable excipient.

As it is used herein, the term "phytosanitary product" refers to all the substances intended for protecting crops and controlling pests and diseases thereof.

As it is used herein, the term "agriculturally acceptable excipient" refers to any substance or combination of substances which can be used in the agricultural sector, and includes any agriculturally acceptable liquid or solid material which can be added to and/or mixed with the microorganism, biologically pure culture or biomass of the invention, in order to have it in a simpler or improved form of application, or with an applicable or desirable activation intensity. Due to the nature of the active ingredient of the agricultural composition (microorganism of the invention), said agriculturally acceptable vehicle has to allow, or not jeopardize or compromise, the viability and the controlling ability of said microorganism.

The phytosanitary product of the invention comprises the microorganism of the invention, the culture of the invention, or the biomass of the invention as a technical active ingredient with nematicidal and/or growth-promoting activity. Said phytosanitary product of the invention corresponds to one or several types of phytosanitary product formulations currently described in the FAO/WHO manual in solid or liquid state comprising wettable powders (WP), oily dispersions (OD), encapsulated granules (CG), capsule suspensions (CS), emulsifiable concentrates or granules (EC/EG), granules (GR), microgranules (MG), microemulsions (ME), water-dispersible granules (WG).

The formulation consists of a suitable amount of technical active ingredient of *Lysobacter enzymogenes* to assure a concentration between $10^3$-$10^{15}$ CFU/g product, mixed with organic or inorganic substances, known as excipients, giving it the technical characteristics necessary for complying with FAO/WHO (phytosanitary or nutritional) standards, and with a solvent or carrier for adjusting the concentration. The excipients comprise ionic or anionic substances with surfactant activity, dispersing activity, wetting activity, drying activity and anti-caking activity, among others. They consist of alkyl-sulfuric esters, alkyl aril sulfonates, alkyl aril ethers, ethoxylated alcohols, ethoxylated fatty acids, polyethylene glycol ethers, acid sugars, potassium salts of fatty acids, sodium salts of fatty acids, carrageenin, carboxymethyl cellulose, xanthan gum, lignosulfonic acid, calcium, magnesium and zinc lignosulfonates, silicon oxide, bentonites, glycerin, magnesium, calcium, aluminum, and iron oxides, among others. The formulation in solid state uses as a carrier or solvent one or several substances such as serite, kaolins, diatomaceous earth, acid earth, bran, monosodium glutamate, glucose, dextrose, lactose, sucrose and the like. The formulation in liquid state uses as a carrier or solvent one or several substances such as vegetable oils, light paraffin oils, polyethylene glycol esters with saturated or unsaturated fatty acids, vegetable glycerin and the like.

The phytosanitary product of the invention can furthermore contain, if desired, other ingredients or constituents commonly used in phytosanitary products such as, but not limited to, solvents, active agents or pH regulators, fertilizers, etc., provided that they all allow or do not jeopardize or compromise viability of the microorganism present in the phytosanitary product. Said ingredients or constituents commonly used in phytosanitary products are generally known by the persons skilled in the art.

The phytosanitary product of the invention can be obtained by conventional methods generally based on mixing suitable amounts of the different components of the agricultural composition.

In a sixth aspect, the invention relates to a supplemented seed, hereinafter supplemented seed of the invention, comprising a seed, and furthermore the microorganism of the invention, or the biologically pure culture of the invention, or the biomass of the invention, or the phytosanitary product of the invention. Said seed can be a seed of any plant of interest in agriculture, forestry, food (for human or animal food), ornamental applications, energetic applications, etc.

In a particular embodiment, the supplemented seed of the invention comprises a seed of a plant of a family selected from Solanaceae, Fabaceae, Malvaceae, Amaranthaceae and Cucurbitaceae. In a more particular embodiment, the supplemented seed of the invention comprises a seed of a plant from the genus *Solanum*. In an even more particular embodiment, the supplemented seed of the invention comprises a seed of a plant from the species *Solanum lycopersicum*. In a still more particular embodiment, the supplemented seed of the invention comprises a seed of a plant from the species *Solanum lycopersicum* "Marmande" variety.

The terms "Solanaceae", "Fabaceae", "Malvaceae", "Amaranthaceae", "Cucurbitaceae", as well as preferred and particular embodiments thereof, have previously been defined in relation to the microorganism of the invention.

The microorganism of the invention can completely or partially cover the seed.

Said supplemented seed of the invention can be obtained by conventional methods; by way of illustration, it can be obtained by submerging the seed in a pure suspension or culture of the microorganism of the invention, or alternatively by spraying said suspension or culture on the seed. Other methods comprise mixing the seed and the microorganism of the invention previously incorporated in an inert solid support that facilitates adhesion of the microorganism of the invention to said seed.

Furthermore, an agricultural-type adhesive containing a suitable concentration of said microorganism, such as an organic-type polymer or gel, such as acacia gum, alginate polymers, methyl cellulose, etc., can be used to improve adhesion of the microorganism of the invention to the seed. Therefore, in a particular embodiment, the supplemented seed of the invention is supported, attached or adhered to an adhesive, such as an agriculturally acceptable adhesive, for example, an organic polymer that is inert for the microorganism of the invention (for example, acacia gum, alginate, methyl cellulose, etc.).

Method for Biologically Controlling a Nematode

In a seventh aspect, the invention relates to a method for biologically controlling a nematode comprising applying to said nematode a microorganism according to the first aspect, a biologically pure culture according to the second aspect, a biomass according to the fourth aspect, or a phytosanitary product according to the fifth aspect.

In a particular embodiment, the nematode is not located in an animal or in a human being. In another embodiment, the nematode is not located in a live animal or in a live human being.

As it is used herein, the term "biologically controlling a nematode" refers to the use of living organisms to control the nematode population, i.e., to control their development, reproduction, number of individuals, etc., either directly (by the action of the organisms used as biological control agents) or indirectly (as a result of the compounds produced by said organisms). Biologically controlling nematodes can involve destroying nematodes or preventing nematodes from developing. As it is used herein, biologically controlling nematodes also covers controlling nematode offspring (development of viable cysts and/or egg masses).

The method according to the seventh aspect comprises applying to the nematode to be biologically controlled a microorganism according to the first aspect, a biologically pure culture according to the second aspect, a biomass according to the fourth aspect, or a phytosanitary product according to the fifth aspect.

The term "nematode" has been previously defined, as have particular and preferred embodiments thereof. In a particular embodiment, the nematode is a plant-parasitic nematode. In a particular embodiment, the nematode is selected from the genera *Meloidogyne, Globodera, Heterodera, Pratylenchus, Tylenchulus, Radophulus* and *Xiphinema*. In an even more particular embodiment, the nematode is selected from the genera *Meloidogyne* and *Globodera*. In a still more particular embodiment, the nematode is *Meloidogyne javanica*.

Contacting the nematode to be biologically controlled with the microorganism, culture, biomass or phytosanitary product of the invention can be carried out by any suitable technique or method, using suitable apparatuses, equipment and devices. The person skilled in the art knows the techniques and methods, as well as suitable apparatuses, equipment and devices for applying biological control agents. The method according to the seventh aspect can be carried out by applying the microorganism, culture, biomass or phytosanitary product of the invention directly on the nematode, in the nematode's habitat, for example in the soil where a plant is going to be or is grown, in the plant susceptible of being attacked by said nematode, or on a seed of a plant susceptible of being attacked by said nematode. The microorganism, culture, biomass or phytosanitary product of the invention can also be applied by means of manual or automated irrigation systems.

In a particular embodiment, the method according to the seventh aspect additionally comprises the use of a fungicide, nematicide or soil insecticide.

As it is used herein, the term "fungicide" refers to agents with the ability to increase mortality or inhibit growth rate of fungi, and also the ability to inhibit germination of fungi spores. Illustrative, non-limiting examples of fungicides include:

Copper compounds: copper chloride, copper oxychloride, cupric oxide, "Bordeaux mixture", copper-8 quinolinolate, basic copper carbonate, copper naphthenate, copper sulfate, copper chromate, copper oleate.

Mercury compounds: Calomel (mercurous chloride), mercuric oxide, mercury lactate, mercuram (phenylmercuric acetate), MEMC (methoxyethyl mercuric chloride), PMA (phenylmercuric acetate).

Tin compounds: fentin acetate (triphenyltin acetate), fentin chloride (triphenyltin chloride), butyltin oxide, Plictran (trichlorohexyltin hydroxide).

Zinc compounds: zinc chloride, chromate, naphthenate and oleate.

Metallic compounds: potassium permanganate, cadmium chloride, ferrous sulfate, neo-asozin (monomethyl ferric arsenate), rhizoctol (methyl arsenic sulfite), urbacid, chrome naphthalene.

Sulfur compounds: sofril, lime sulfur.

Organophosphorous compounds: pyrazophos, IBP/kitazin, edifenphos, ditalimfos.

Dithiocarbamates: zineb, maneb, mancozeb, nabam, thiram, ferbam, bunema, vapam, metiram, methylmetiram.

Carbamates: thiophanate, thiophanate-methyl.

Halogenated hydrocarbons: 1,1-dichloromethane, dibromomethane, bromomethane, chloropicrin, carbon tetrachloride, p-dichlorobenzene, hexachlorobenzene, chloroneb, dodecyl ammonium bromide, hexachlorophene, pentachlorophenol, isobac (hexachlorophene monosodium salt), etc.

Aromatic nitro compounds: dinitrophenol, nitrodiphenyl, DNOC (4,6-dinitro-o-cresol), dinobuton, tecnazene, binapacryl, dinocap, nirit, brassicol (pentachloronitrobenzene), etc.

Quinines: chloranil, dichlone, benzoquinone, dithianon, etc.

Anilides: benodanil, pyrocarbolid, carboxin, oxycarboxin, salicylanilide, etc.

Guanidine compounds: dodine (dodecylguanidine acetate), guazatine, etc.

Phthalimides: folpet, captan, captafol, chlorothalonil, dimetakion, etc.

Pyrimidines: dimethirimol, ethirimol, bupirimate, etc.

Thiodiazoles: dazomet, terrazole, milneb, etc.

Triazines: anilazine, triadimefon, etc.

Isoxazolones: hymexazol, drazoxolon, etc.

Imidazoles: glyodin, bencmil, thiabendazole, triforine, carbendazim, etc.

Other heterocyclic compounds: tridemorph, chinomethionate, etc.

Antibiotics: blasticidin, gliotoxin, griseofulvin, polyoxin, phytobacteriomycin, kasugamycin, validamycin, etc.

Oils: anthracene, ammonium naphthenate, etc.

Aldehydes, ketones, oxides: formaldehyde, p-formaldehyde, allyl alcohol, ethylene oxide, propylene oxide, etc.

Plant extracts: marketed as plant strengtheners or OPPM (Other plant protection means).

Others: rhodamine, Trapex® (methyl isocyanate), dichlofuanid, fenaminosulf, etc.

Biological products: *Trichoderma* (Tusal®), *Streptomyces* (Actinovate®), etc.

As it is used herein, the term "nematicide" refers to agents with the ability to inhibit egg hatching and/or paralyze larval forms in any of their stages and/or adult forms or to prevent nematodes from developing. Illustrative, non-limiting examples of nematicides which can be used in the method for biologically controlling a nematode include:

Fumigants: D-D (mixture of 1,2-dichloropropane and 1,3-dichloropropene); ethylene dibromide; 1,2-dibromo-3-chloropropane; methyl bromide; chloropicrin (nitrochloroform); metam sodium (sodium methyldithiocarbamate); Dazomet (3,5-dimethyl-1,3,5-thiadiazinan-2-thione); methyl isothiocyanate (MITC); sodium tetrathiocarbonate.

Carbamates: aldicarb (2-methyl-2-(methylthio)propanal O-(N-methylcarbamoyl)oxime); aldoxicarb ([(E)-(2-methyl-2-methylsulfonylpropylidene)amino] N-methylcarbamate); carbofuran (2,2-dimethyl-2,3-dihydro-1-benzofuran-7-yl methylcarbamate); oxamyl (methyl 2-(dimethylamino)-N-[(methylcarbamoyl)oxy]-2-oxoethanimidothioate).

Organophosphates: ethoprop (0-'ethyl S,S-dipropylphosphorodithioate); fenamiphos (tyl-3-methyl-4-(methylthio)phenyl(1-methylethyl)phosphoramidate)); cadusafos (O-ethyl S,S-di-sec-butyl phosphorodithioate); fosthiazate ((RS)—S-sec-butyl O-ethyl 2-oxo-1,3-thiazolidin-3-ylphosphonothioate); thionazin (O,O-Diethyl O-2-pyrazinyl phosphorothioate); fosthietan (diethyl 1,3-dithiethan-2-ylidenephosphoramidate); isazophos (O-5-chloro-1-isopropyl-1H-1,2,4-triazol-3-yl O,O-diethyl phosphorothioate).

Biochemical agents: DiTera® (mixture of compounds produced by the nematode-parasitic fungus *Myrothecium verrucaria*), Cladosan® (product obtained from exoskeletons of crab and lobsters, rich in chitin and urea), Sincoin® (mixture of extracts of prickly pear Opuntia *lindheimeri*, oak *Quercus falcata*, sumac *Rhus aromatica*, and mangrove Rhizophora mangle).

Biological products: spores of the fungus *Paecilomyces lilacinus* (BioAct®, Biostat®), *Bacillus firmus* (Flocter®).

As it is used herein, the term "soil insecticide" refers to an agent able to kill, control and/or repel insects the life cycle of which includes a stage in soil. Illustrative, non-limiting examples of soil insecticides include: Aldrin (hexachlorohexahydro-endo-exodimethane naphthalene); Dieldrin (hexachloroepoxy-octahydro-endo-exo-dimethanonaphthalene); Chlorodane (octachloro-4,7-methanotetrahydro-indane); Temik® (Aldicarb: 2-methyl-2-(methylthio)propanal-O-(N-methylcarbamoyl)oxime); Carbofuran (2,3-dihydro-2,2-dimethyl-7-benzofuran methyl carbamate); Landrin® (trimethyl phenyl methylcarbamate); Chlorfenvinphos (2-chloro-1-(2,4-dichlorophenyl)vinyl diethyl phosphate); Phorate® (0,0-diethyl-S-[(ethylthio)methyl] phosphorodithioate); Terburox® (S-tert-butylthiomethyl-O-O-diethyl phosphorodithioate); biological products such as fungus *Beauveria bassiana* (Botanigard®, Naturalis®), spores of the fungus *Paecilomyces* fumosoroseus (NoFly®, PreFeRal®), *Bacillus thuringiensis* (Dipel®) and the like.

Method for Preventing Plant Infection Caused by a Nematode and Method for Treating a Plant Infected by a Nematode In an eighth aspect, the invention relates to a method for preventing plant infection caused by a nematode, comprising applying an effective amount of a microorganism according to the first aspect, a biologically pure culture according to the second aspect, a biomass according to the fourth aspect, or a phytosanitary product according to the fifth aspect on said plant, on the seed of said plant, in the soil surrounding said plant or on a nematode susceptible of infecting said plant, or alternatively planting a seed of said plant supplemented with a microorganism according to the first aspect, a biologically pure culture according to the second aspect, a biomass according to the fourth aspect, or a phytosanitary product according to the fifth aspect.

As it is used herein, the expression "preventing plant infection caused by a nematode" refers to any activity preventing, impeding, holding up or delaying plant infection caused by a nematode.

The term "nematode" has been previously defined. In a preferred embodiment, the nematode is a plant-parasitic nematode. In a more preferred embodiment, the plant-parasitic nematode is selected from the genera *Meloidogyne, Globodera, Heterodera, Pratylenchus, Tylenchulus* and *Radophulus*. In an even more particular embodiment, the plant-parasitic nematode is from the genus *Meloidogyne*. In a still more particular embodiment, the plant-parasitic nematode is *Meloidogyne javanica*.

As it is used herein, the term "plant" refers to any living being belonging to the kingdom Plantae (sensu strictissimo) including eukaryotic living beings with photosynthetic ability, without locomotor ability, and the cell walls of which are mainly made up of cellulose. In sensu strictissimo, the term Plantae includes the clade Embrophyta (land plants: vascular and non-vascular (bryophytes)) comprising: hepaticas, hornwort, moss, lycopodiophyta and plants with seeds (gymnosperms and angiosperms). In the present invention this term refers to species of the taxon Angiospermae.

In a particular embodiment, the plant belongs to a family selected from Solanaceae, Musaceae, Fabaceae, Malvaceae, Amaranthaceae, Vitaceae, Rutaceae, Cucurbitaceae, Poaceae, Rubiaceae, ornamental plant families or a family of fruit trees. All these families, as well as particular embodiments thereof, have previously been described.

In a preferred embodiment, the plant belongs to the family Solanaceae. In a more preferred embodiment, the plant from the family Solanaceae belongs to the genus *Solanum*. In an even more preferred embodiment, the plant from the genus *Solanum* is *Solanum lycopersicum*. In a still more preferred embodiment, the plant from the genus *Solanum* is *Solanum lycopersicum* "Marmande" variety. The terms "*Solanum*", "*Solanum lycopersicum*" and "*Solanum lycopersicum* "Marmande" variety" have previously been described.

The prevention of plant infection caused by a nematode can be carried out on the plant once it has been planted or on the seed of said plant before it is planted. Therefore, the method according to the eighth aspect comprises the following alternatives:

(i) Applying an effective amount of the microorganism, biologically pure culture, biomass or phytosanitary product of the invention on said plant, on the seed of said plant, in the soil surrounding said plant or on a nematode susceptible of infecting said plant.

As it is used herein, the term "effective amount" refers to the amount necessary for stabilizing, impeding, holding up or delaying progression of stages of development of the nematode in question in the plant, and thereby obtaining beneficial or desired results. The term "effective amount" refers to the minimum amount of microorganism in total CFU, regardless of whether it is in the form of a culture, biomass or phytosanitary product formulation. The effective amount of the microorganism, biologically pure culture, biomass or phytosanitary product which can be applied on the plant for preventing, delaying or reducing infection caused by a nematode can vary within a broad range interval and be determined by the person skilled in the art taking into account the type of plant and the type of nematode, among other factors. In a particular embodiment, the plant is from the family Solanaceae, preferably a plant from the genus *Solanum*, even more preferably from the species *Solanum lycopersicum*, even more preferably from the "Marmande" variety, and the nematode is a nematode from the genus *Meloidogyne*, more preferably from the species *Meloidogyne javanica*, in which case the effective amount of the microorganism of the invention is comprised between $1\times10^5$ CFU and $1\times10^{12}$ CFU, preferably between $1\times10^8$ CFU and $1\times10^{11}$ CFU.

The effective amount can be applied in a single administration or in several administrations. When it is applied in several administrations, said administrations can be 3, 4, 5, 6, 7, 8, 9 or 10 applications in which application 4 is applied 10-20 days after application 3, and more preferably 15-20 days after application 3. In a particular embodiment, the effective amount of the microorganism, biologically pure culture, biomass or phytosanitary product of the invention is carried out in several applications: it is applied in a first application before transplanting the plant, in a second application after transplanting the plant, and at least a number "n" of applications, wherein "n" is an integer comprised between 1 and 10, wherein each of said "n" applications is applied between 10 and 20 days after the preceding application, more preferably between 15 and 20 days after the preceding application.

In an even more particular embodiment, the effective amount of the microorganism, biologically pure culture, biomass or phytosanitary product of the invention is performed in three applications: a first application before transplanting the plant, a second application after transplanting, and the third application after the second application. In a more particular embodiment, the second application is performed between 10 and 20 days after transplanting, preferably 15 days after transplanting. In an even more particular embodiment, the effective amount of the microorganism, biologically pure culture, biomass or phytosanitary product of the invention is performed in four applications: a first application before transplanting the plant, a second application after transplanting the plant, a third application after the second application and a fourth application after the third application. In a still more particular embodiment, the third application is performed between 10 and 20 days after the second application, preferably 15 days after the second application. In a still more particular embodiment, the fourth application is performed between 10 and 20 days after the third application, preferably 15 days after the third application.

The effective amount of the microorganism, biologically pure culture, biomass or phytosanitary product of the invention can be applied on the plant, on the seed of the plant, in the soil surrounding the plant or on a nematode susceptible of infecting the plant.

If it is applied on the plant, the application can be made on the entire plant or on some parts of the plant, for example, at the base of the stem, in the area occupied by the roots, tubercles and bulbs. The effective amount of the microorganism, biologically pure culture, biomass or phytosanitary product of the invention can be applied on the plant by any suitable technique or method, using suitable apparatuses, equipment and devices. The person skilled in the art knows the techniques and methods, as well as suitable apparatuses, equipment and devices for applying biological control agents on plants. In a particular embodiment, the microorganism, culture or biomass of the invention is formulated in the form of a phytosanitary product suitable for administration to a plant by any conventional technique or method and using any conventional device, for example, by spraying, dusting, or by any other suitable agricultural administration method, for example by means of baiting, incorporating into the soil or in automated or manual irrigation systems.

The application can also take place on the seed of the plant. As it is used herein, the term "seed" refers to any resting stage of a plant that is physically separated from the vegetative phase of the plant and/or that can be stored for more or less prolonged periods of time and/or that can be used to make another individual plant of the same species grow again. In this case, the application can be done before or while the seed is planted in the soil. The person skilled in the art knows suitable techniques for administering a biological control agent such as the microorganism, culture, biomass or phytosanitary product of the invention to a seed of a plant.

The application can also take place in the soil surrounding the plant. In a particular embodiment, administration is performed close to the neck of the root of the plant. The person skilled in the art knows suitable techniques for administering a biological control agent such as the microorganism, culture, biomass or phytosanitary product of the invention to the soil surrounding a plant.

The application can also take place on a nematode susceptible of infecting the plant. In that case, the application of the microorganism, culture, biomass or phytosanitary product of the invention on the nematode susceptible of infecting the plant is carried out by contacting said nematode with the microorganism, culture, biomass or phytosanitary product of the invention by means of any of the techniques or methods described in relation to the method for biologically controlling a nematode according to the seventh aspect.

(ii) Planting a seed of said plant supplemented with a microorganism, biologically pure culture, biomass or phytosanitary product of the invention.

The seed that has been supplemented with a microorganism, biologically pure culture, biomass or phytosanitary product of the invention has previously been described.

As it is used herein, the term "planting" refers to placing a seed in prepared terrain so that it germinates, giving rise to the development of a plant. The supplemented seed of the invention can be planted by means of any suitable technique for planting seeds of a plant. Said techniques are known by the person skilled in the art.

In a ninth aspect, the invention relates to a method for treating a plant infected by a nematode comprising applying an effective amount of a microorganism according to the first aspect, a biologically pure culture according to the second aspect, a biomass according to the fourth aspect, or a phytosanitary product according to the fifth aspect on said plant or in the soil surrounding said plant.

As it is used herein, the expression "treating a plant infected by a nematode" refers to performing any activity aimed at holding up, stopping or reducing progression of the infection caused by a nematode, or improving at least one symptom of said infection. Holding up or stopping progression of the infection is understood to mean obtaining beneficial or desired results, including but not limited to reducing symptoms, reducing disease duration, stabilizing pathological states (specifically for preventing additional impairment), delaying progression of the disease, improving the pathological state and remission (both partial and complete). Control of progression of the disease also involves prolonging survival, compared with the survival that is expected if treatment is not applied.

The terms "plant", "nematode" and "effective amount" have previously been described. The methods for applying the microorganism, culture, biomass or phytosanitary product of the invention on the plant or in the soil surrounding the plant have previously been described.

The particular embodiments of the method of the eighth aspect also apply to the ninth aspect.

In a particular embodiment, the plant treated by means of the method of the ninth aspect belongs to the family Solanaceae.

In a particular embodiment of the method of the ninth aspect, the effective amount of a microorganism according to the first aspect, a biologically pure culture according to the second aspect, a biomass according to the fourth aspect, or a phytosanitary product according to the fifth aspect is applied a first time before transplanting the plant and a second time after transplanting the plant.

In a particular embodiment, the method according to the eighth or ninth aspect additionally comprises the use of a fungicide, nematicide or soil insecticide. The terms "fungicide", "nematicide" and "soil insecticide", as well as particular embodiments thereof, have previously been described.

Method for Stimulating Plant Growth

In a tenth aspect, the invention relates to a method for stimulating plant growth comprising applying an effective amount of a microorganism according to the first aspect, a biologically pure culture according to the second aspect, a biomass according to the fourth aspect, or a phytosanitary product according to the fifth aspect on said plant, on the seed of said plant or in the soil surrounding said plant, or alternatively planting a seed of said plant supplemented with a microorganism according to the first aspect, a biologically pure culture according to the second aspect, a biomass according to the fourth aspect, or a phytosanitary product according to the fifth aspect.

As it is used herein, the expression "stimulating plant growth" refers to the ability to facilitate or stimulate development of the plant root system, stem growth, plant blooming, etc. The plant growth-promoting activity by the microorganism of the invention can be determined by the person skilled in the art by means of any assay in which a parameter related to plant growth, such as height, root dry weight or fresh weight, aerial dry weight or fresh weight, etc., in the presence or absence of the microorganism of the invention is determined as previously described.

The term "plant", as well as particular and preferred embodiments thereof, has previously been described.

Stimulating plant growth can be carried out on the plant once it has been planted or on the seed of said plant before it is planted. Therefore, the method according to the tenth aspect comprises the following alternatives:
(i) Applying an effective amount of the microorganism, biologically pure culture, biomass or phytosanitary product of the invention on said plant, on the seed of said plant or in the soil surrounding said plant.

As it is used herein, the term "effective amount" refers to the amount necessary for producing the desired effect in the plant, specifically, stimulating or promoting plant growth. The term "effective amount" refers to the minimum amount of total CFU microorganism regardless of whether it is in the form of a culture, biomass or phytosanitary product formulation. The effective amount of the microorganism, biologically pure culture, biomass or phytosanitary product which can be applied on the plant for promoting the growth of said plant can vary within a broad range interval and be determined by the person skilled in the art taking into account the type of plant, among other factors. In a particular embodiment, the plant is from the family Solanaceae, preferably a plant from the genus *Solanum*, even more preferably from the species *Solanum lycopersicum*, even more preferably from the "Marmande" variety, in which case the effective amount of the microorganism of the invention is comprised between $1 \times 10^7$ CFU and $1 \times 10^{12}$ CFU, preferably between $1 \times 10^8$ CFU and $1 \times 10^{11}$ CFU.

The effective amount can be applied in a single administration or in several administrations, as previously described in relation to the method for preventing plant infection caused by a nematode.

The effective amount of the microorganism, biologically pure culture, biomass or phytosanitary product of the invention can be applied on the plant, on the seed of the plant or in the soil surrounding the plant as previously described in relation to the method for preventing plant infection caused by a nematode.
(ii) Planting a seed of said plant supplemented with a microorganism, biologically pure culture, biomass or phytosanitary product of the invention.

The seed that has been supplemented with a microorganism, biologically pure culture, biomass or phytosanitary product of the invention has previously been described.

The term "planting" also has previously been described.

In a particular embodiment, the method according to the tenth aspect additionally comprises the use of a fungicide, nematicide, soil insecticide or plant growth promoter. The terms "fungicide", "nematicide" and "soil insecticide", as well as particular embodiments thereof, have previously been described.

As it is used herein, the term "plant growth promoter" refers to an agent that is able to stimulate plant growth and therefore help the plant to resist against other pests and/or diseases. Illustrative, non-limiting examples of plant growth promoters include: *Azotobacter chrococcum* and *Bacillus megaterium*; *Azotobacter vinelandii*; *Azotobacter vinelandii*, *Bacillus licheniformis* and *Bacillus megaterium*; *Bacillus licheniformis*; *Bacillus licheniformis* plus *Bacillus pumilus*; *Bacillus pumilus*; *Bacillus* sp.; *Bacillus velezensis*; *Formononetin*; *Lactobacillus* and other bacteria; *Paecilomyces lilacinus*; *Pseudomonas fluorescens* plus *Pseudomonas púitida*; *Trichoderma hamatum* plus *Trichoderma koningii*; *Trichoderma hamatum* plus *Trichoderma longibrachiatum*; *Trichoderma harzianum*; *Trichoderma koningii* plus bacteria of the rhizosphere; *Trichoderma viride*; Bionema Plus®; Biobalance®.

EXAMPLES

The following examples illustrate the invention and must be considered in an illustrative and non-limiting sense thereof.

Example 1

Production and Characterization of *Lysobacter enzymogenes* Strain MR B25

Production

*Lysobacter enzymogenes* strain MR B25 was isolated from a pepper plant harvested from/coming from a field managed according to ecological agriculture practices located in Gavá, Barcelona, in September 2011.

For isolation, the roots were disinfected on the surface by immersion in a 5% sodium hypochlorite solution for 5 minutes and 3 subsequent washings in sterile distilled water. Disinfection was verified by seeding in Petri dishes with Potato Dextrose Agar culture medium (PDA: potato extract, 4 g/L; dextrose, 20 g/L; agar 15 g/L) and nutritive agar (NA:

meat extract, 1 g/L, yeast extract 2 g/L, soy peptone 5 g/L, sodium chloride 5 g/L and agar 15 g/L). Once disinfected, they were subjected to mechanical disruption in phosphate buffer by means of a previously sterilized mortar. The resulting solution was filtered through a Kitasato flask to remove root fragments. Then serial dilutions from $10^0$ to $10^{-5}$ were performed and they were seeded in PDA, NA and CZAPEK (Sucrose (30 g/L), NaNO$_3$ (3 g/L), MgSO$_4$.7H$_2$O (0.5 g/L), KCl (0.5 g/L), FeSO$_4$.7H$_2$O (0.01 g/L), K$_2$HPO$_4$ (1 g/L) and Agar (13.5 g/L)) plates. These plates were incubated in an incubator at 26° C. and observed daily. Each of the colonies that grew (bacteria or fungi) was seeded again in new plates with the same medium from which they came until obtaining pure cultures of the selected microorganisms. Finally, the isolates were separated from the medium by scraping the plate in soy peptone with 10% glycerol, giving rise to generation 0 of each microorganism, which was stored at −80° C.

Characterization

The strain has been characterized at the morphological and molecular level. For morphological characterization, the bacterium was incubated in general medium [nutritive agar (NA)] at 2 temperatures (26° C. and 32° C.) and colony characteristics were observed.

Morphological Characterization:

*Lysobacter enzymogenes* strain MR B25 is a gram-negative bacillus. It has a colony with a diameter of 3 mm after 96 hours of growth in Petri dishes with NA medium in a bacteriological incubator at a constant temperature of 26° C. The resulting colonies are medium-sized, round colonies with little relief and slightly rugose. When grown at 26° C., the colonies have an opaque appearance with a creamy yellow color, whereas at 32° C. it forms bright yellow colonies in the center with an outer cream-colored ring (FIG. 1).

Molecular Characterization:

The molecular identification of *Lysobacter enzymogenes* strain MR B25 was performed by means of amplifying 16S ribosomal DNA sub-unit with the use of the primers:

```
                                      (SEQ ID NO: 1)
FORWARD:   8-f      (AGTTTGATCCTGGCTCAG)
and (SEQ ID NO: 2)
REVERSE:   1492-r   (ACGGTTACCTTGTTACGACTT).
```

The search for matching sequences was performed using BLAST (Basic Local Alignment Search Tool) software and the results showed that the amplified sequence was within the species *Lysobacter enzymogenes*.

The sequence obtained from the fragment amplified by these primers (SEQ ID NO: 3) is shown below:

```
                                         (SEQ ID NO: 3)
CGGCAGCACAGNGGAGCTTGCTCCTTGGGTGGCGAGTGGCGGACGGGTGA

GGAATACGTCGGAATCTGCCTATTTGTGGGGGATAACGTAGGGAAACTTA

CGCTAATACCGCATACGACCTACGGGTGAAAGTGGGGGACCGCAAGGCCT

CACGCAGATAGATGAGCCGACGTCGGATTAGCTAGTTGGCGGGGTAAAGG

CCCACCAAGGCGACGATCCGTAGCTGGTCTGAGAGGATGATCAGCCACAC

TGGAACTGAGACACGGTCCAGACTCCTACGGGAGGCAGCAGTGGGGAATA

TTGGACAATGGGCGCAAGCCTGATCCAGCCATGCCGCGTGTGTGAAGAAG
```

-continued

```
GCCTTCGGGTTGTAAAGCACTTTTGTCCGGAAAGAAAAGCTTAGGGTTAA

TAACCTTGAGTCATGACGGTACCGGAAGAATAAGCACCGGCTAACTTCGT

GCCAGCAGCCGCGGTAATACGAAGGGTGCAAGCGTTACTCGGAATTACTG

GGCGTAAAGCGTGCGTAGGTGGTTTGTTAAGTCTGATGTGAAAGCCCTGG

GCTCAACCTGGGAATGGCATTGGAAACTGGCTTACTAGAGTGCGGTAGAG

GGTAGCGGAATTCCCGGTGTAGCAGTGAAATGCGTAGATATCGGGAGGAA

CATCTGTGGCGAAGGCGGCTACCTGGACCAGCACTGACACTGAGGCACGA

AAGCGTGGGGAGCAAACAGGATTAGATACCCTGGTAGTCCACGCCCTAAA

CGATGCGAACTGGATGTTGGGGGCAACTTGGCCCTCAGTATCGAAGCTAA

CGCGTTAAGTTCGCCGCCNGGGAAGTACGGTCGCAAGACTGAAACTCNNG

GAATTGACGGGGCCNGCACAAGCGGTGGAGTATGTGGTTTAATTCNATG

CANCGCGAAGAACCTTACCTGGCCTTGACNTGTCGAGAACTTTNCA
```

Example 2

In Vitro Nematicidal Activity of *Lysobacter enzymogenes* Strain MR B25 Against *Meloidogyne javanica* Eggs Materials and Methods Assay on Eggs The in vitro nematicidal ability of bacterium *L. enzymogenes* strain MR B25 on *M. javanica* eggs was evaluated in hatching chambers (Nunclon™Surface multiwell plates, Nunc, Denmark) in which 2 g of previously sterilized soil had been added. The substrate was then inoculated with an aqueous suspension containing 350 *M. javanica* eggs. The biological control agent *L. enzymogenes* strain MR B25 was applied at $1 \times 10^{10}$ CFU/mL.

The hatching chamber was incubated at 26° C. for 3 weeks and periodic readings were taken 24 hours after applying the biological control agent and 1, 2 and 3 weeks later to determine the hatching percentage. Eight repetitions of each treatment, a negative control with a reference chemical at the commercially recommended dose (0.0125% Nemacur®; active ingredient: fenamiphos) and a control with sterile distilled water to establish a reference for the results to the normal hatching percentage were included.

Results and Discussion

TABLE 1

Efficacy (%) corrected with respect to the control of the chemical used as a reference and *L. enzymogenes* strain MR B25 against *M. javanica* eggs.

| Treatments | Efficacy (%) |
|---|---|
| Nemacur ® (Fenamiphos) | 67.59 |
| *L. enzymogenes* MR B25 | 80.70 |

Figure 2:
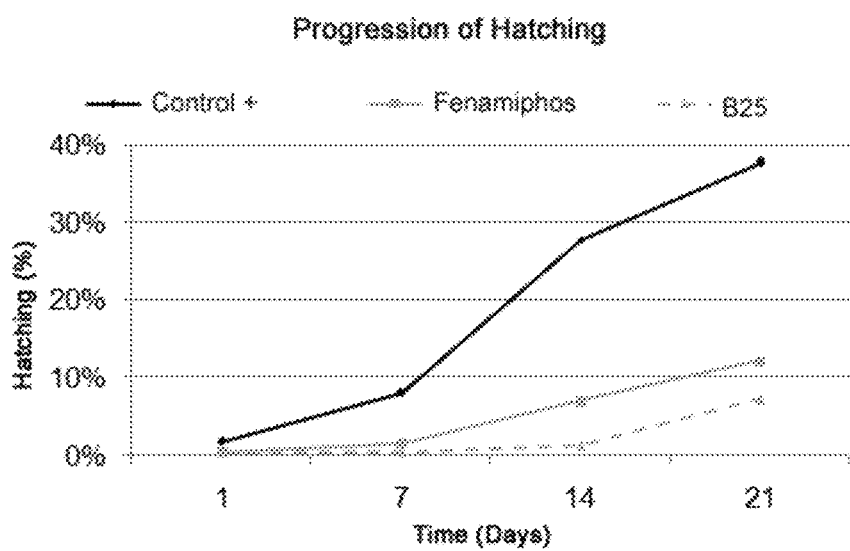
FIG. 2. Progression of *M. javanica* egg hatching in the control and in treatments with the reference chemical (fenamiphos) and with *L. enzymogenes* strain MR B25 at different readings (days).

In the follow-up for the hatching of *M. javanica* eggs for the 21 days the assay lasted, treatment with *L. enzymogenes* strain MR B25 showed a significant reduction with respect to the control (FIG. 2).

Three weeks after applying the different treatments, 37.55% of the untreated eggs (control) hatched, whereas 7.25% of those treated with *L. enzymogenes* strain MR B25 hatched and 12.17% of those treated with Nemacur® (reference chemical) hatched.

Figure 3:
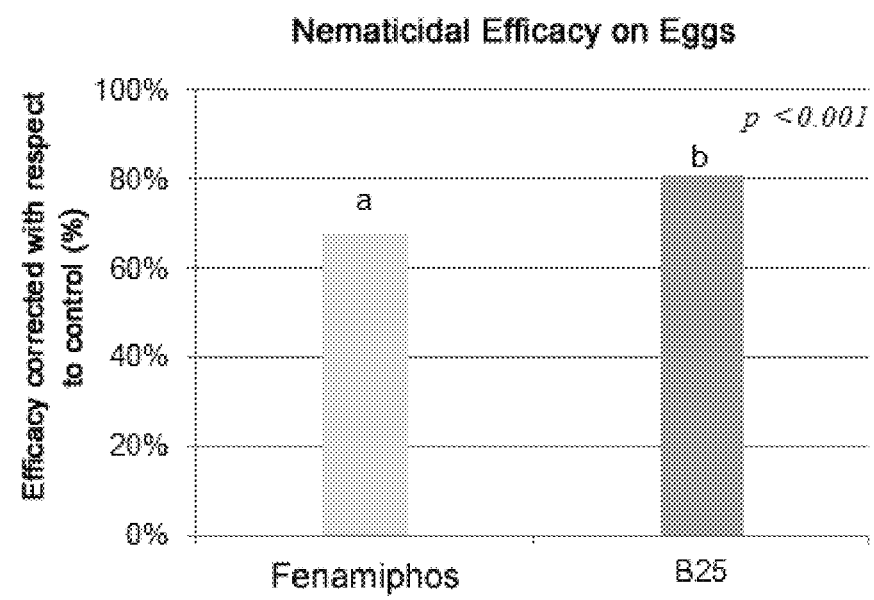
FIG. 3. Nematicidal activity on *M. javanica* eggs of *L. enzymogenes* strain MR B25 and the reference chemical (fenamiphos) corrected with respect to the control. The different letters indicate statistically significant differences.

Therefore, *L. enzymogenes* strain MR B25 has 80.70% efficacy in reducing hatching with respect to the control under in vitro conditions, whereas in the reference chemical, efficacy in reducing hatching was 67.59%, i.e., 13.11% less than with a microorganism object of the present invention (*L. enzymogenes* strain MR B25) (FIG. 3).

Example 3

In Vitro Nematicidal Activity of *Lysobacter enzymogenes* Strain MR B25 Against *Meloidogyne Javanica* Juveniles
Materials and Methods The nematicidal ability of bacterium *L. enzymogenes* strain MR B25 was evaluated in vitro against *M. javanica* eggs in hatching chambers (Nunclon™Surface multiwell plates, Nunc, Denmark), in which 2 g of previously sterilized soil were added. An aqueous suspension containing 200 juvenile forms of *M. javanica* was then added, and the biological control agent, *L. enzymogenes* strain MR B25, was applied at $1\times10^{10}$ CFU/mL (1E+10 CFU/mL). The hatching chamber was incubated at 26° C. for 7 days and counts were performed by means of the Hawksley® chamber after 24 hours (1 day) and after 7 days to determine the number of live juveniles (% mortality). A control with sterile distilled water and another control with a reference chemical (Nemacur® 0.0125%: active ingredient=fenamiphos) were included. Eight repetitions of each treatment were performed.
Results and Discussion

TABLE 2

Efficacy (%) corrected with respect to the control of *L. enzymogenes* MR B25 and of the chemical used as a reference against *M. javanica* juveniles.

| Treatments | Efficacy (%) | |
|---|---|---|
| | 1 day | 7 days |
| Nemacur ® (Fenamiphos) | 96.72 | 100 |
| *L. enzymogenes* MR B25 | 95.62 | 100 |

Figure 4:
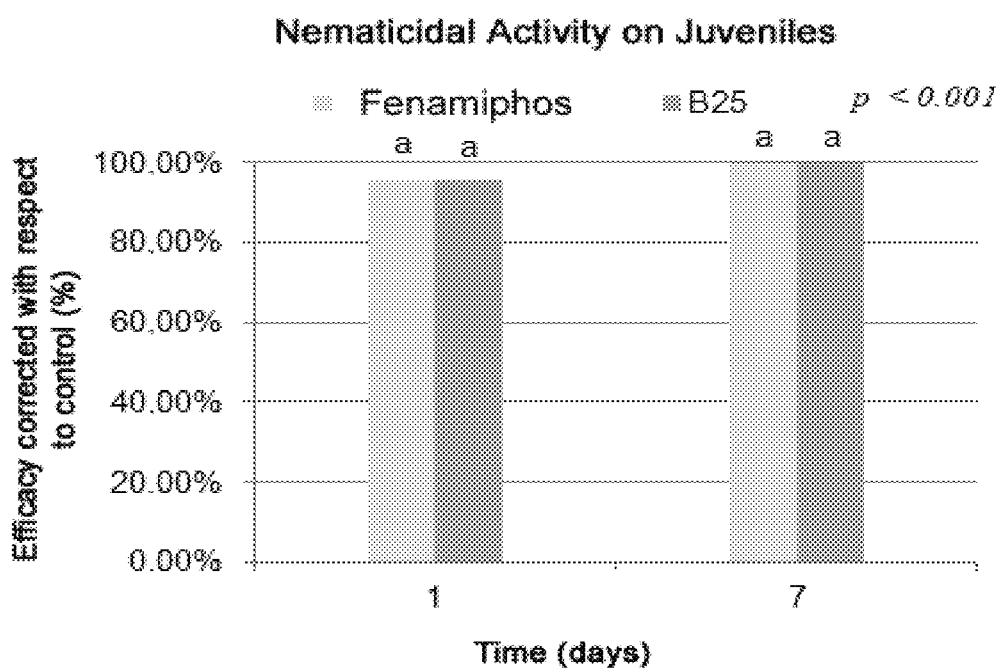
FIG. 4. Nematicidal activity on *M. javanica* juveniles (J$_2$) of *L. enzymogenes* strain MR B25 and the reference chemical (fenamiphos). The different letters indicate statistically significant differences.

*L. enzymogenes* strain MR B25 shows juvenile mortality percentages corrected with respect to the control in the order of 96% 24 hours after application. There are no significant differences with respect to the reference chemical used (FIG. 4).

Example 4

Comparison of In Vitro Nematicidal Activity of *Lysobacter enzymogenes* Strain MR B25 and Strain B322 Against *Meloidogyne javanica* Eggs
Materials and Methods
Assay on Eggs The nematicidal ability of bacterium *L. enzymogenes* strain MR B25 and of *L. enzymogenes* strain B322 were evaluated in vitro against *M. javanica* eggs in hatching chambers (Nunclon™Surface multiwell plates, Nunc, Denmark), in which 2 g of previously sterilized soil were added. An aqueous suspension corresponding to 650 *M. javanica* eggs was then added, and biological control agents *L. enzymogenes* strain MR B25 and *L. enzymogenes* strain B322 were applied at a concentration of $2.96\times10^{10}$ CFU/mL (2.96E+10 CFU/mL) and $2.86\times10^{10}$ CFU/mL (2.86E+10 CFU/mL), respectively. The hatching chamber was, incubated at 26° C. for 7 days and counts were performed by means of the Hawksley® chamber 24 hours and 1, 2, 3 and 4 weeks after applying the biological control agents to determine the hatching percentage. A control with sterile distilled water and another control with a reference chemical (Nemacur® 0.0125%; active ingredient: fenamiphos) were included. Eight repetitions of each treatment were performed.
Results and Discussion

TABLE 3

Comparison of the efficacy (%) corrected with respect to the control of two *L. enzymogenes* strains, MR B25 and B322 and of the chemical used as a reference.

| Treatments | Efficacy (%) |
|---|---|
| Nemacur ® (Fenamiphos) | 62.03% |
| *L. enzymogenes* MR B25 2.96E+10 | 59.80% |
| *L. enzymogenes* B322 2.86E+10 | 25.17% |

Figure 5:
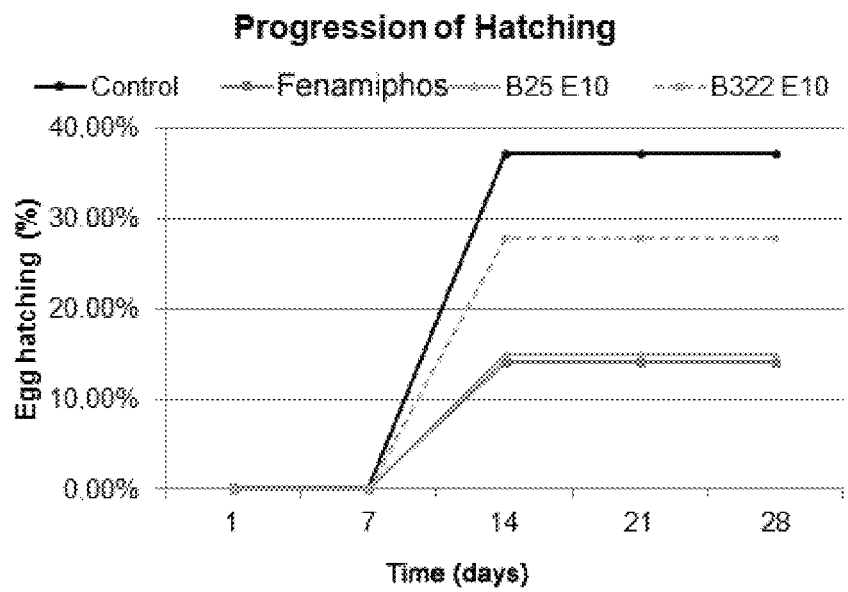
FIG. 5. Progression of the *M. javanica* egg hatching in eggs treated with 2 different *L. enzymogenes* strains (MR B25 and B322) compared with the control and the reference chemical (fenamiphos).

The data on progression of hatching for the 28 days the experiment lasted shows clear differences between both *L. enzymogenes* strains (FIG. 5). Strain MR B25 has control levels in the order of the chemical used as a reference, whereas strain B322 has levels closer to the untreated control.

Figure 6:
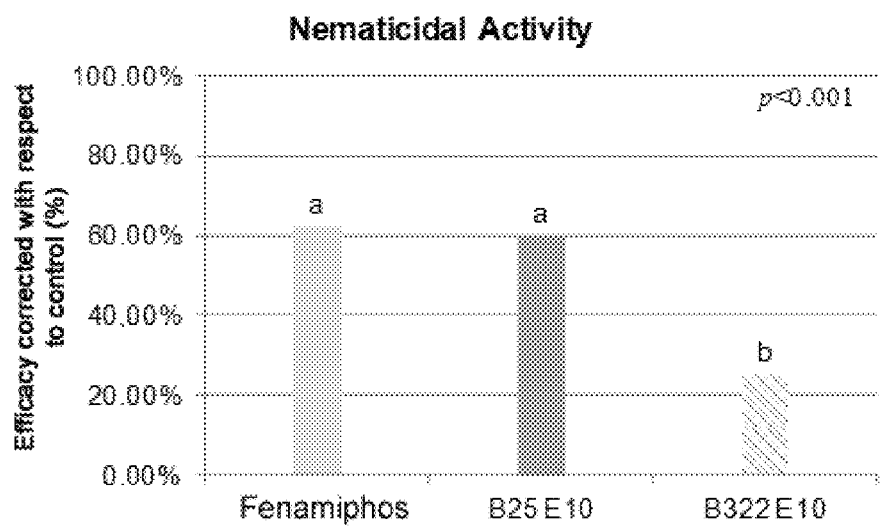
FIG. 6. Nematicidal efficacy percentage of 2 *L. enzymogenes* strains (MR B25 and B322) compared with the reference chemical (fenamiphos) corrected with respect to the control. The different letters indicate statistically significant differences.

The percentage of efficacy obtained by strain MR B25 has no statistically significant differences with respect to the chemical used as a reference while it does with respect to the other *L. enzymogenes* strain (B322) used for this assay, which shows a percentage of efficacy of 25% (FIG. 6), almost 35% less than the strain object of this invention. As demonstrated by the results of this experiment, the high nematicidal effect of *L. enzymogenes* strain MR B25 is not a property of all strains of the species *L. enzymogenes*, but rather is characteristic of strain MR B25 object of the present invention.

Example 5

Comparison of the In Vitro Nematicidal Activity of *Lysobacter enzymogenes* Strain MR B25 and Strain B322 and their Respective Metabolites Against *Meloidogyne javanica* Eggs
Materials and Methods The objective of this assay was to verify that the nematicidal activity of *L. enzymogenes* MR B25 is a feature characteristic of the strain and not the species, in addition to demonstrate that the action of control on phytopathogenic nematodes is fundamentally due to the microorganism and not to the possible metabolites released into the medium by the microorganism.

After 24 hours of growth of *L. enzymogenes* strain MR B25 and B322 in LB medium under optimal growth conditions of the species, the biomass was separated by means of centrifugation, the pellet of both strains being obtained. Then the supernatants of both cultures were sterilized through filtration in a Kitasato flask by means of a 0.2 μm filter to remove any bacterial cell that may have remained in the broth.
Assay on Eggs The nematicidal ability of bacterium *L. enzymogenes* strain MR B25 and strain B322 and their respective metabolites was evaluated in vitro against *M. javanica* eggs in hatching chambers (Nunclon™Surface multiwell plates, Nunc, Denmark), in which 2 g of previously sterilized soil were added. A concentration corresponding to 500 *M. javanica* eggs was then added. Four treatments were assayed: 2 of these treatments were performed with the *L. enzymogenes* strain MR B25 and *L. enzymogenes* strain B322 pellets, at a concentration of $6.8 \times 10^8$ CFU/mL (6.8E+08 CFU/mL) and $3.2 \times 10^8$ CFU/mL (3.2E+08 CFU/mL), respectively, and the other 2 treatments were performed with the metabolites obtained from fermentation of both strains, in which 200 µL of the solution was added. The hatching chamber was incubated at 26° C. for 7 days and counts were performed by means of the Hawksley® chamber 24 hours and 1, 2, 3 and 4 weeks after applying the treatments to determine the nematode egg hatching percentage. A control with sterile distilled water and another control with the sterile culture medium used for the growth of the bacteria were included. Six repetitions of each treatment were performed.

Results and Discussion

TABLE 4

Efficacies obtained in the different treatments corrected with respect to their corresponding controls.

| Treatments | Efficacy (%) |
| --- | --- |
| *L. enzymogenes* MR B25 Biomass 6.8E+08 | 30.24 |
| *L. enzymogenes* B322 Biomass 3.2E+08 | 12.47 |
| *L. enzymogenes* MR B25 metabolites | 9.08 |
| *L. enzymogenes* B322 metabolites | 4.58 |

Figure 7:
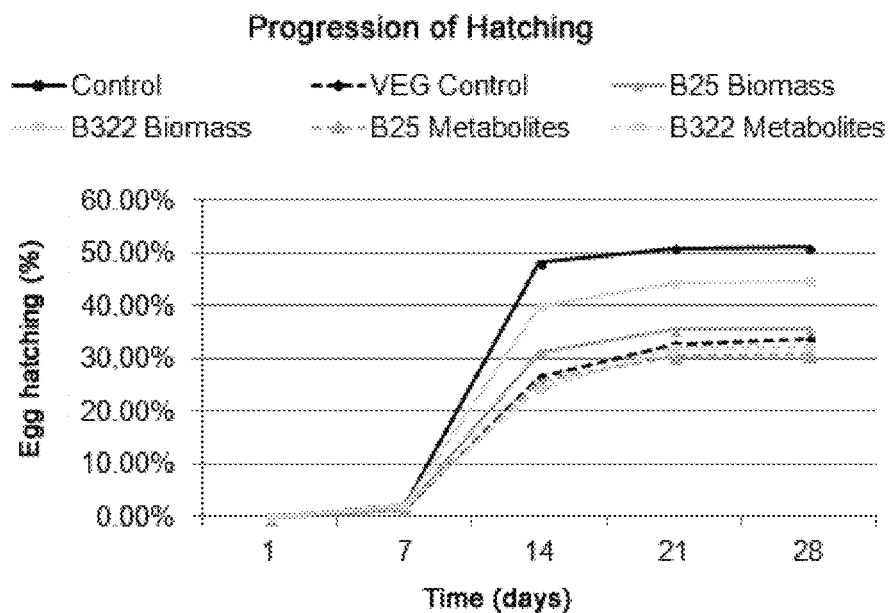
FIG. 7. Progression of *M. javanica* egg hatching in eggs treated with the biomass and the metabolites of 2 different *L. enzymogenes* strains (MR B25 and B322) compared with the control of sterile distilled water and sterile culture medium (VEG control).

The data on progression of hatching shows differences between *L. enzymogenes* MR B25 and the control and *L. enzymogenes* strain B322 after day 7. In the case of the metabolites, when the results are compared with the control culture medium (VEG control), differences are not observed at any point of the experiment (FIG. 7).

Figure 8:
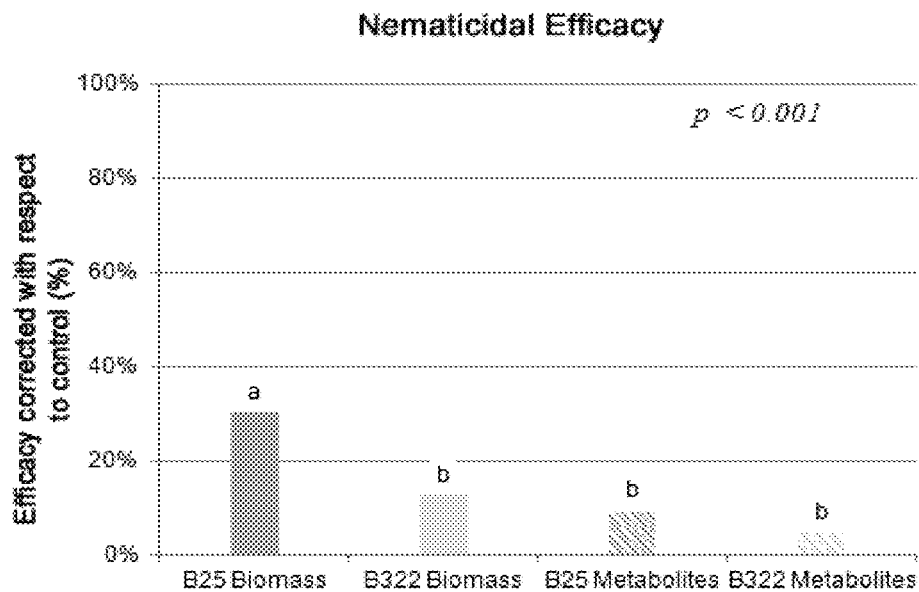
FIG. 8. Nematicidal efficacies on *M. javanica* eggs obtained by the biomass of *L. enzymogenes* strains MR B25 and B322 and by their metabolites corrected with respect to the corresponding controls. The different letters indicate statistically significant differences.

The biomass of *L. enzymogenes* MR B25 shows an efficacy of 30% in controlling *M. javanica*, with statistically significant differences with respect to the efficacy obtained by the biomass of strain B322 (Table 4 and FIG. 8). In turn, the metabolites obtained from fermentation of both strains show percentages of efficacy corrected with respect to the control of the culture medium (VEG control) less than those obtained by the biomass corrected with respect to the control. This can be because the nematicidal action of strain MR B25 is due to the microorganism and not to the possible substances released into culture medium used, also showing statistically significant differences between the efficacy obtained by the biomass of *L. enzymogenes* MR B25 and its metabolites.

According to the results obtained in this assay, it can be inferred that nematicidal action is fundamentally exerted by the microorganism and not by its metabolites, although said metabolites can be part of the microorganism mode of action. It is again demonstrated that this activity cannot be attributed to all strains of the species *L. enzymogenes*.

Example 6

In Vivo Nematicidal Activity of *Lysobacter enzymogenes* Strain MR B25 Against *Meloidogyne javanica*

Materials and Methods

The in vivo nematicidal ability of bacterium *L. enzymogenes* strain MR B25 was evaluated in the "Marmande" tomato variety against *M. javanica* juveniles. Each treatment consisted of 12 repetitions and each one was inoculated with 1,000 juveniles. The assay schedule is as follows:

TABLE 5

*Lysobacter enzymogenes* strain MR B25 application plan in an in vivo assay against *M. javanica*

| Day 0 | Day 3 | Day 4 | Day 11 | Day 21 |
| --- | --- | --- | --- | --- |
| Preventive treatment | Transplant | Nematode inoculation | $1^{st}$ Application | $2^{nd}$ Application |

The plants were placed in 1,000 cm³ pots and treated with 10 mL of an aqueous solution containing *L. enzymogenes* strain MR B25 in the preventive treatment and with 15 mL in the $1^{st}$ and $2^{nd}$ applications after transplant.

The microorganism concentrations used for treatment were:

TABLE 6

Concentration of the aqueous solution containing *L. enzymogenes* strain MR B25 in each application.

| Concentration | Preventive treatment | $1^{st}$ Application | $2^{nd}$ Application |
| --- | --- | --- | --- |
| CFU/mL | 5.5E+08 | 4.8E+08 | 4.8E+08 |

The reference chemical was 1.2% Nemacur® (fenamiphos). A control with sterile distilled water was also included.

The assay lasted for 2 months. After said time, the different parameters were evaluated to verify nematicidal activity of the microorganism:
Reproduction: No. eggs/g root
Fertility: No. eggs/mass
Infectiveness: No. masses/plant
Height
Aerial fresh weight
Root fresh weight The evaluation of the last 3 parameters also helps to determine the plant growth-promoting ability of the microorganism, if any.

Results and Discussion

TABLE 7

Efficacy (%) in reproduction, fertility and infectiveness obtained by *L. enzymogenes* MR B25 and the chemical control corrected with respect to the control.

| TREATMENTS | Reproduction Efficacy (%) | Infectiveness Efficacy (%) | Fertility Efficacy (%) |
| --- | --- | --- | --- |
| Nemacur® (Fenamiphos) | 91.94 | 80.52 | −41.06 |
| *L. enzymogenes* MR B25 | 73.81 | 64.95 | 69.54 |

Figure 9:
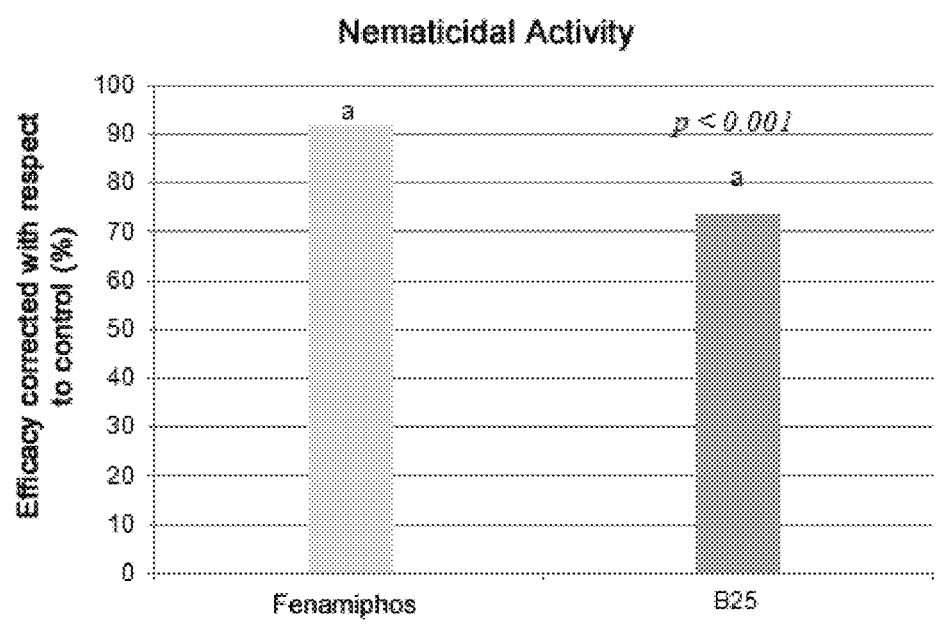
FIG. 9. Nematicidal efficacy of *L. enzymogenes* strain MR B25 and the reference chemical (fenamiphos) on *M. javanica* eggs and juveniles in tomato plants.

The results obtained in this assay show that *L. enzymogenes* strain MR B25 has nematicidal activity against *M. javanica* comparable to that of the chemical control used as a reference, with an efficacy of 73.81% (FIG. 9). Both treatments have statistically significant differences with respect to the control.

Figure 10:
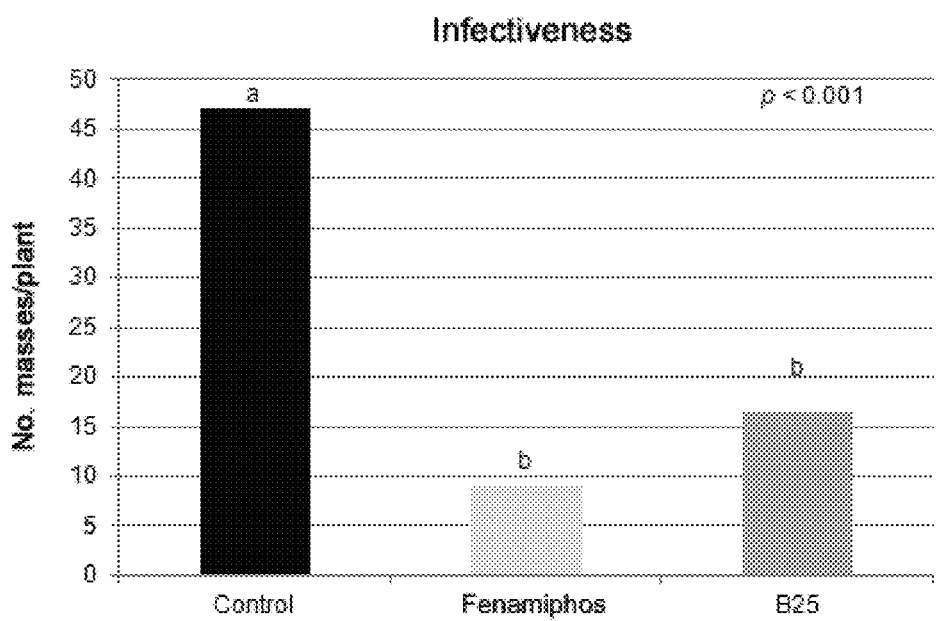
FIG. 10. Infectiveness of the *M. javanica* adults treated with *L. enzymogenes* strain MR B25 and with the reference chemical (fenamiphos) compared with infectiveness of the control. The different letters indicate statistically significant differences.
Figure 11:
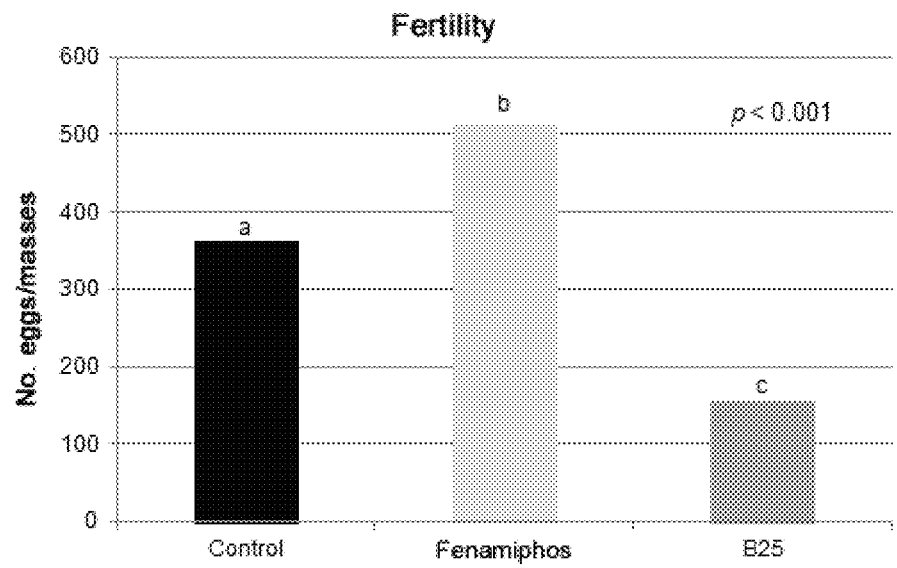
FIG. 11. Fertility of *M. javanica* females treated with *L. enzymogenes* strain MR B25 and the reference chemical (fenamiphos) compared with the control. The different letters indicate statistically significant differences.

In addition, the data on fertility and infection, which is used to determine the action of the microorganism in *M. javanica* adults, also shows statistically significant differences with respect to the control. *L. enzymogenes* MR B25 reduces the number of masses formed by adult females in the root in addition to the number of eggs in each mass, thereby also reducing the ability of the parasite to cause infection (FIGS. 10 and 11).

Figure 12:
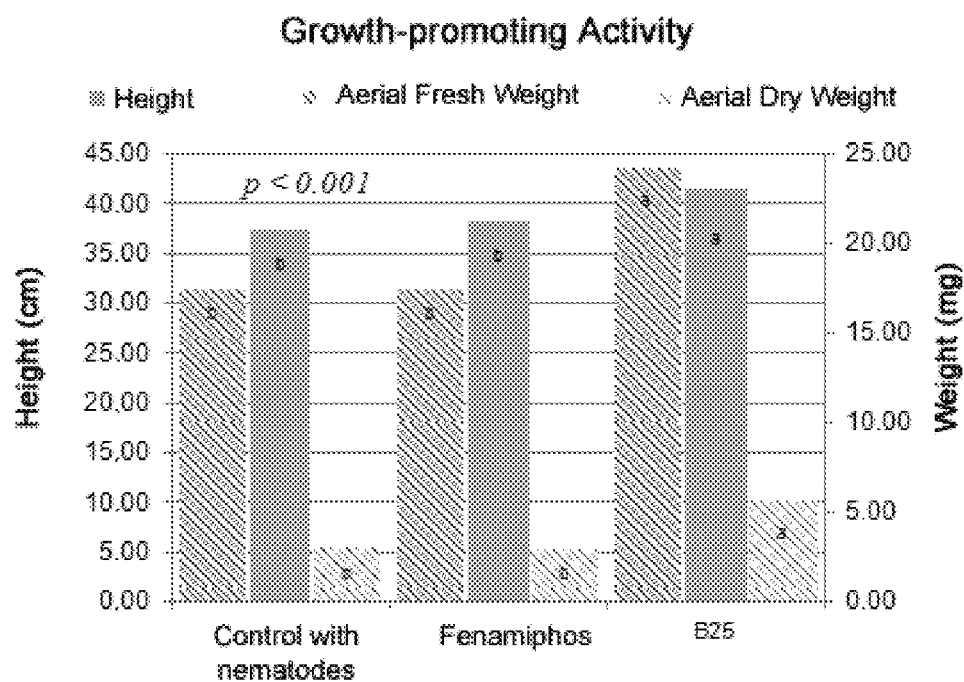
FIG. 12. Growth-promoting activity of *L. enzymogenes* strain MR B25 in tomato, compared with growth-promoting activity of the control and with growth-promoting activity of a reference chemical (fenamiphos). The different letters indicate statistically significant differences.

Furthermore, important growth-promoting activity is demonstrated both in height and in the aerial biomass, with statistically significant differences with the absolute control and the reference chemical for all the parameters evaluated (FIG. 12).

Example 7

In Vivo Nematicidal Activity of Different Doses of *Lysobacter enzymogenes* Strain MR B25 Against *Meloidogyne javanica*

Materials and Methods

The nematicidal ability of bacterium *L. enzymogenes* strain MR B25 at different doses was evaluated in vivo in tomato plants from the "Marmande" variety against *M. javanica* juveniles "Murcia" population. Each treatment consisted of 10 repetitions and each of them was inoculated with 900 juveniles. The assay schedule was as follows:

TABLE 8

*L. enzymogenes* strain MR B25 application plan in an in vivo assay against *M. javanica*

| Day 0 | Day 3 | Day 4 | Day 11 | Day 21 |
|---|---|---|---|---|
| Preventive treatment | Transplant | Nematode inoculation | 1st treatment | 2nd treatment |

The plants were placed in 1,000 cm³ pots and treated with 10 mL of a solution with *L. enzymogenes* strain MR B25 in the preventive treatment and with 15 mL in the 1st and 2nd treatments after transplanting.

The treatments are detailed below:

TABLE 9

Summary of treatments applied in the assay.

| Treatment | Type | 1st Application | 2nd Application | 3rd Application |
|---|---|---|---|---|
| Control | Sterile distilled water | — | — | — |
| BIOSTAT® 0.2 g/plant | Reference formulation | 0.2 g/plant | 0.2 g/plant | 0.2 g/plant |
| *L. enzymogenes* MR B25 1 × 10⁸ CFU/mL | Technical grade active ingredient | 7.1 × 10⁸ (7.10E+08) | 5.50 × 10⁸ (5.50E+08) | 3.10 × 10⁸ (3.10E+08) |
| *L. enzymogenes* MR B25 1 × 10⁷ CFU/mL | Technical grade active ingredient | 8.40 × 10⁷ (8.40E+07) | 7.40 × 10⁷ (7.40E+07) | 2.40 × 10⁷ (2.40E+07) |
| *L. enzymogenes* MR B25 1 × 10⁶ cfu/mL | Technical grade active ingredient | 7.90 × 10⁶ (7.90E+06) | 6.10 × 10⁶ (6.10E+06) | 2.40 × 10⁶ (2.40E+06) |

The reference product applied was BIOSTAT® WP at 0.2 g/plant, a biopesticide product formulated from spores of fungus *Purpureocillium lilacinum* strain PL11, and a control with sterile distilled water was included.

Two months after the first application, the different parameters were evaluated to verify nematicidal and growth-promoting activity, if any:

Reproduction: No. eggs/g root
Height
Aerial fresh weight

Results and Discussion

TABLE 10

Table showing results of nematicidal efficacy of *L. enzymogenes* B25 at different doses corrected with respect to the control.

| Treatments | % Efficacy |
|---|---|
| Biostat ® WP 0.2 g/plant | 41.26% |
| *L. enzymogenes* MR B25 7.10E+08 | 43.49% |
| *L. enzymogenes* MR B25 8.40E+07 | 25.87% |
| *L. enzymogenes* MR B25 7.90+E06 | −5.17% |

Figure 13:
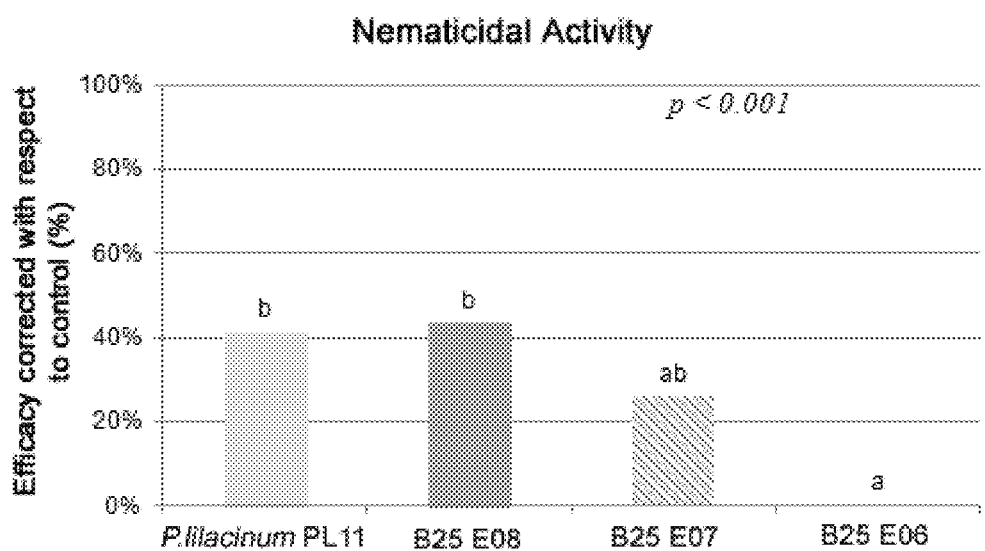
FIG. 13. Nematicidal activity on *M. javanica* of *L. enzymogenes* strain MR B25 at different doses and of the reference biological product (*Purpureocillium lilacinum* PL11) corrected with respect to the control. The different letters indicate statistically significant differences.

The nematicidal activity of *L. enzymogenes* MR B25 is dose-dependent as shown in FIG. 13, where it can be concluded that the effective dose of *L. enzymogenes* MR B25 is 1×10⁸ CFU/mL. There are no statistically significant differences between treatment with *L. enzymogenes* MR B25 and with the biological product used as a reference (FIG. 13).

Figure 14:
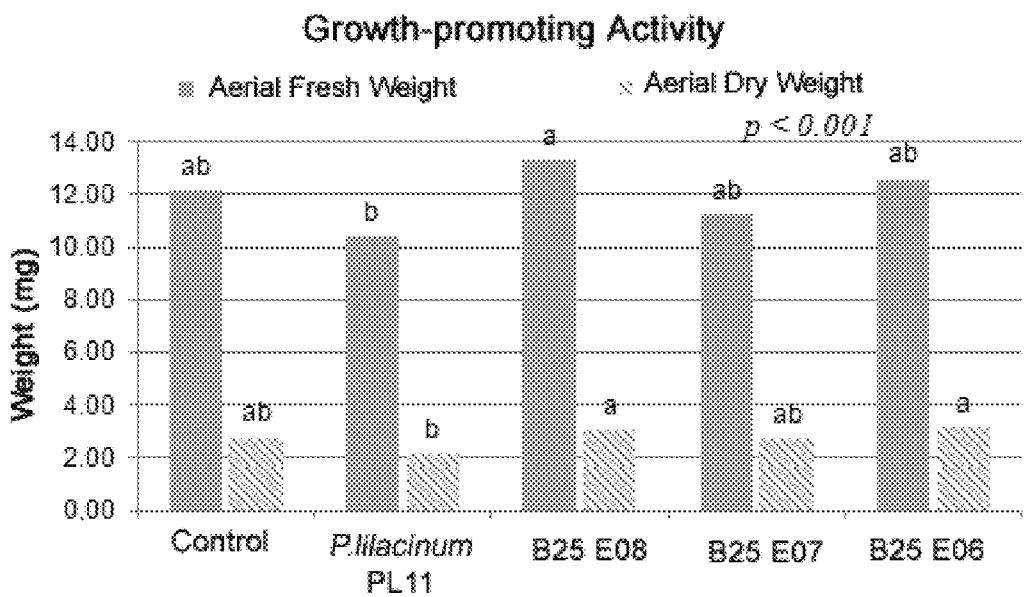
FIG. 14. Growth-promoting activity (aerial fresh weight and aerial dry weight) of the plant treated with *L. enzymogenes* MR B25 at different doses and of the plant treated with the reference biological product (*P. lilacinum* PL11) compared with growth-promoting activity of the control. The different letters indicate statistically significant differences.

The results obtained in this assay again demonstrate the growth-promoting ability of bacterium *L. enzymogenes* MR B25. In the assessment of aerial fresh and dry weights, an increase in biomass is observed in the plants treated with the bacterium at the different evaluated doses (FIG. 14).

Example 8

Comparison of the In Vivo Nematicidal Activity of *Lysobacter enzymogenes* Strain MR B25 and Strain B322 Against *Meloidogyne javanica* Juveniles Materials and Methods The nematicidal ability of bacterium *L. enzymogenes* strain MR B25 and strain B322 was evaluated in vivo in tomato plants from the "Marmande" variety against *M. javanica* juveniles "Seville" population. Each treatment consisted of 10 repetitions and each of them was inoculated with 1,600 juveniles. The assay schedule was as follows:

TABLE 11

*L. enzymogenes* strain MR B25 application plan in an in vivo assay against *M. javanica*

| Day 0 | Day 3 | Day 4 | Day 11 | Day 21 |
|---|---|---|---|---|
| Preventive treatment | Transplant | Nematode inoculation | $1^{st}$ treatment | $2^{nd}$ treatment |

The plants were placed in 1,000 cm³ pots and treated with 10 mL of a solution with *L. enzymogenes* strain MR B25 and with *L. enzymogenes* strain B322 in the preventive treatment and with 15 mL in the $1^{st}$ and $2^{nd}$ treatments after transplant.

The treatments are detailed below:

TABLE 12

Summary of the treatments applied in the assay

| Treatment | Type | Dose 1st Application | 2nd Application | 3rd Application |
|---|---|---|---|---|
| CONTROL | Sterile distilled water | — | — | — |
| BIOSTAT ® | Reference formulation | 0.2 g/plant $1 \times 10^7$ | 0.2 g/plant $1 \times 10^7$ | 0.2 g/plant $1 \times 10^7$ |
| L. enzymogenes MR B25 $1 \times 10^8$ | PELLET | $3.20 \times 10^8$ (3.20E+08) | $2.10 \times 10^8$ (2.10E+08) | $3.30 \times 10^8$ (3.30E+08) |
| L. enzymogenes B322 $1 \times 10^8$ | PELLET | $2.36 \times 10^8$ (2.36E+08) | $2.70 \times 10^8$ (2.70E+08) | $3.80 \times 10^8$ (3.80E+08) |

The reference product applied was BIOSTAT® WP at 0.2 g/plant, a biopesticide product formulated from spores of *Purpureocillium lilacinum* PL11, and a control with sterile distilled water was included.

The assay lasted for 2 months, after which time the following parameters were evaluated:
Reproduction: No. eggs/g root
Fertility: No. eggs/mass
Infectiveness: No. masses/plant
Results and Discussion

TABLE 13

Results of the nematicidal activity of *L. enzymogenes* strain MR B25 compared with strain B322

| Treatments | Efficacy |
|---|---|
| BIOSTAT ® (*P. lilacinum* PL11) | 38.20% |
| *L. enzymogenes* MR B25 | 37.41% |
| *L. enzymogenes* B322 | 4.24% |

Figure 15:
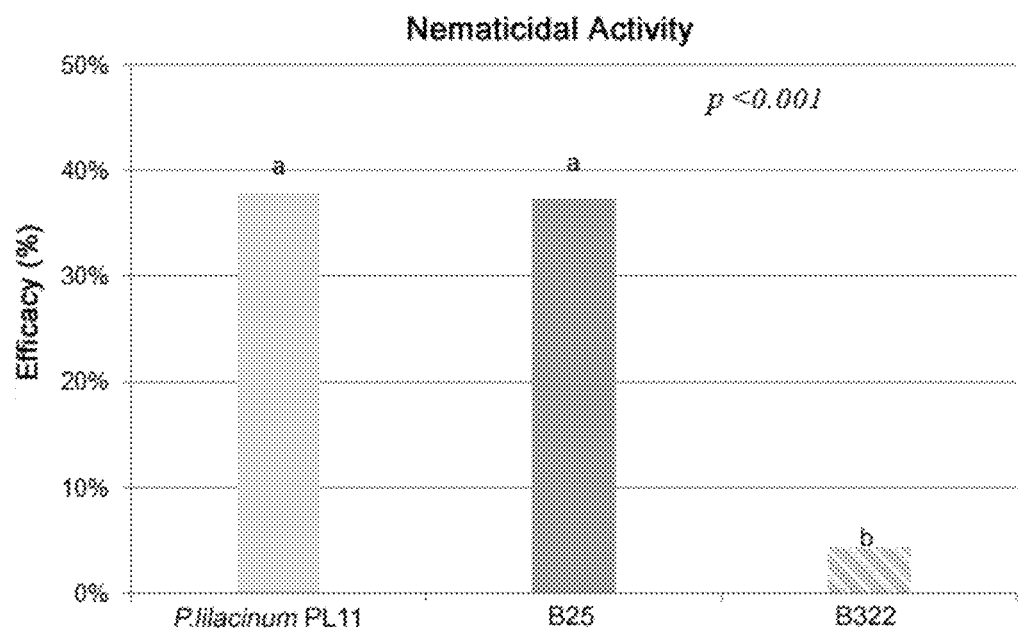
FIG. 15. Nematicidal activity on *M. javanica* of 2 *L. enzymogenes* strains (MR B25 and B322) and the reference biological product (*P. lilacinum* PL11) corrected with respect to the control. The different letters indicate statistically significant differences between treatments.

*L. enzymogenes* strain B25 has an efficacy of almost 40% (FIG. 15) over control of phytopathogenic nematode *M. javanica* in this assay, showing statistically significant differences against the other *L. enzymogenes* strain (B322) evaluated, demonstrating that the nematicidal activity of *L. enzymogenes* MR B25 is characteristic of the strain and not the species. Furthermore, it shows no statistically significant differences with respect to the biological product used as a reference. The percentages of efficacy obtained in this assay are slightly less than those obtained in previous assays due to the greater pathogen pressure used (1,600 juveniles compared with the 900 juveniles inoculated in other assays).

Figure 16:
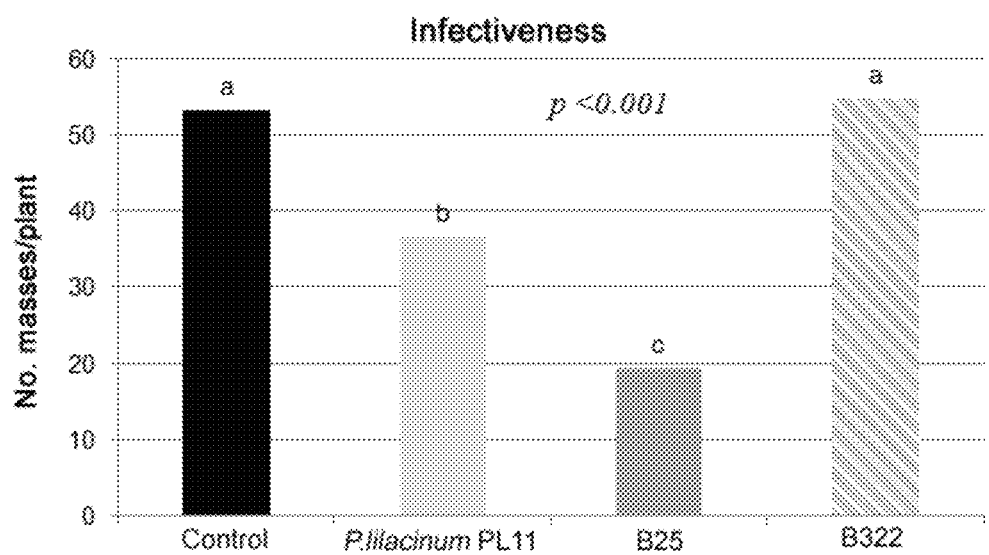
FIG. 16. Infectiveness of the *M. javanica* adults treated with 2 *L. enzymogenes* strains (MR B25 and B322) and the reference biological product (*Purpureocillium lilacinum* PL11) compared with the control. The different letters indicate statistically significant differences.
Figure 17:
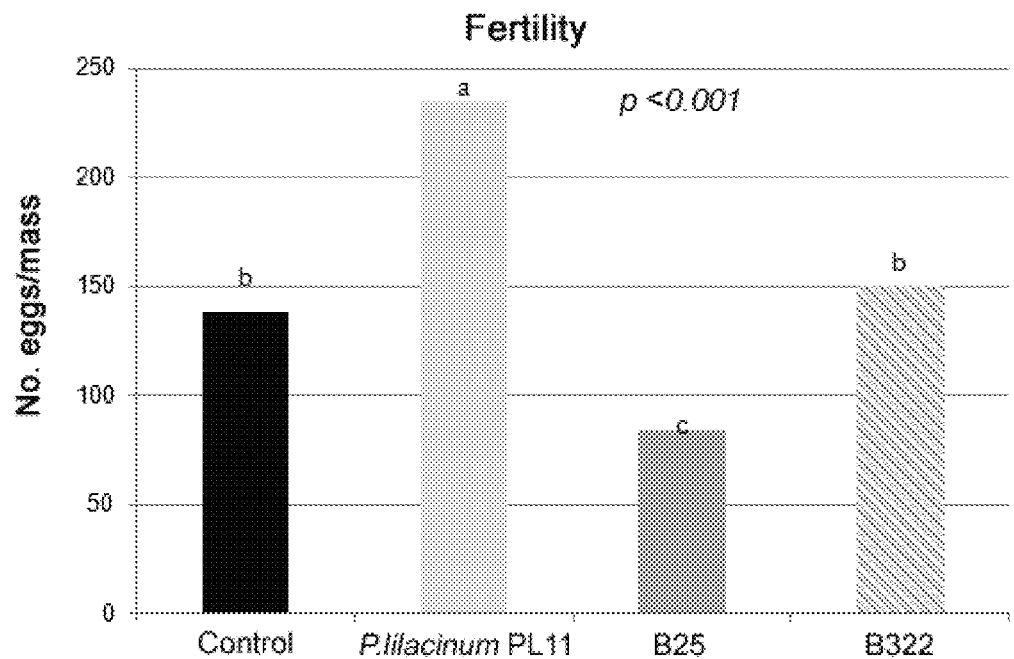
FIG. 17. Fertility of *M. javanica* females treated with 2 *L. enzymogenes* strains (MR B25 and B322) and the reference biological product (*P. lilacinum* PL11) compared with fertility of the control. The different letters indicate statistically significant differences.

Analysis of data on infectiveness and fertility shows that *L. enzymogenes* MR B25 considerably reduces the number of masses/plant and the number of eggs/mass, thereby reducing the ability of *M. javanica* to cause infection. The data shows that there are statistically significant differences with respect to the other *L. enzymogenes* strain used (B322) and with respect to *P. lilacium* PL11 (FIGS. 16 and 17).

Example 9

In Vivo Growth-Promoting Activity of *Lysobacter enzymogenes* Strain MR B25 in Tomato Plants
Materials and Methods To evaluate growth-promoting ability, 25 tomato seeds from the "Marmande" variety were planted in trays with cells having a mL capacity, with depleted substrate (peat at 10% and vermiculite:perlite (3:1)). They were deposited in a climatic chamber under controlled light, temperature and moisture conditions until completing the cotyledon stage, at which time technical grade active ingredient of *L. enzymogenes* MR B25 was applied at a concentration of $2.83 \times 10^7$ CFU/mL (2.83 E+07 CFU/mL) in a total volume of 5 mL/cell (=seed). Absolute control of sterile distilled water was furthermore included. The assay lasted for 2 months. After this time period, the plants of the treatment and control were processed to evaluate the following parameters:
Height
Aerial fresh weight
Root fresh weight
Aerial dry weight
Root dry weight
Results and Discussion

Figure 18:
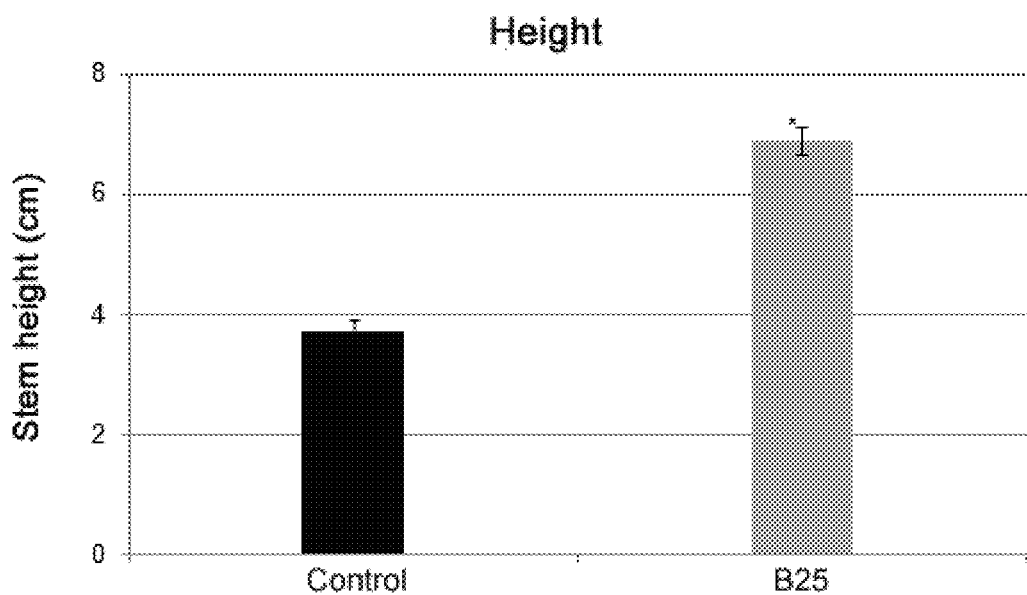
FIG. 18. Stem height in plants treated with *L. enzymogenes* MR B25 compared with the control. The column marked with an asterisk (*) indicates statistically significant differences with respect to the control.
Figure 19:
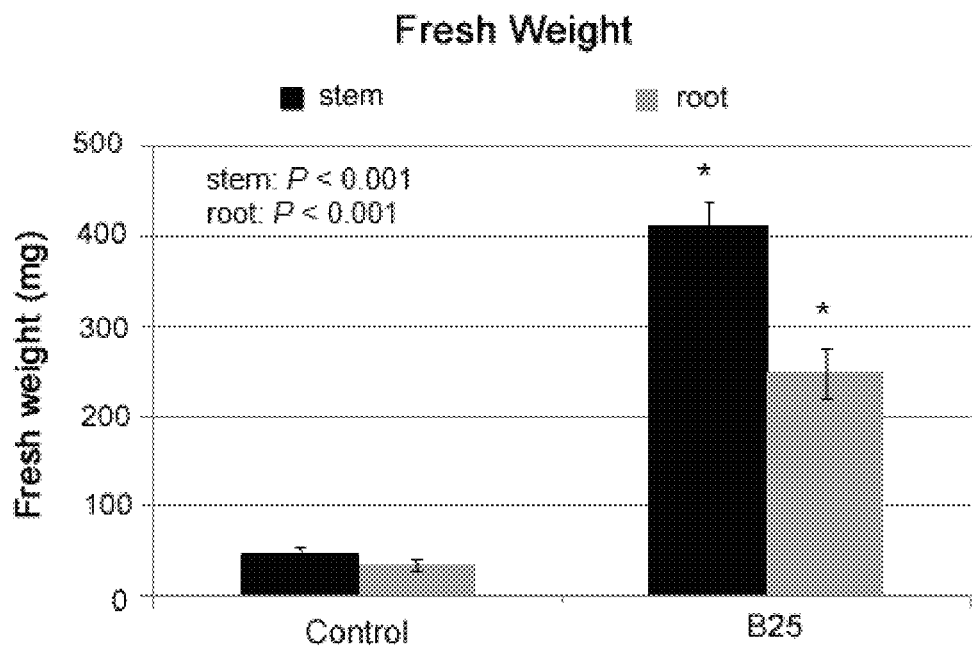
FIG. 19. Aerial and root fresh weight of the plant treated with *L. enzymogenes* MR B25 compared with the control. The columns marked with an asterisk (*) indicate statistically significant differences with respect to the control.
Figure 20:
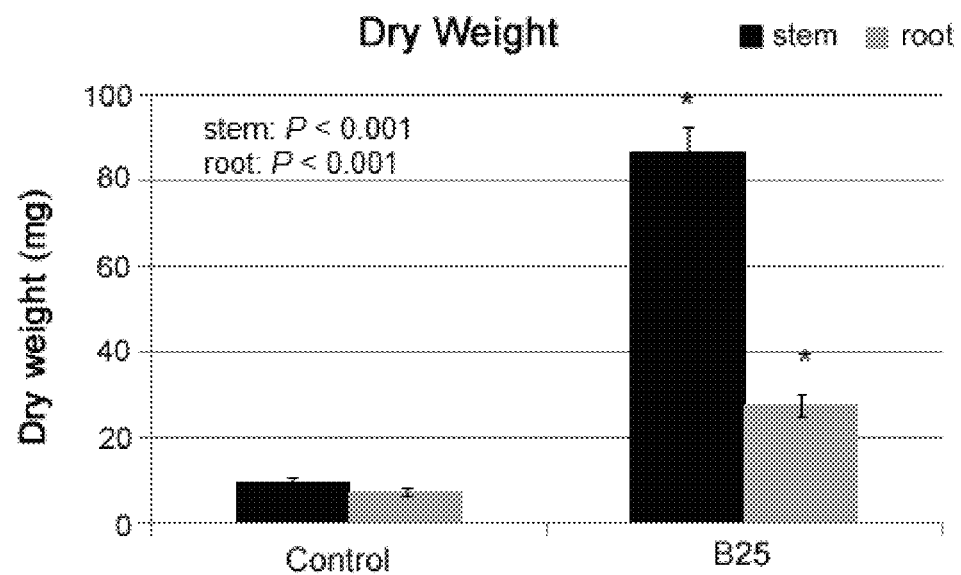
FIG. 20. Aerial and root dry weight of the plant treated with *L. enzymogenes* MR B25 compared with the control. The columns marked with an asterisk (*) indicate statistically significant differences with respect to the control.

*L. enzymogenes* strain MR B25 promotes plant growth with statistically significant differences with respect to the control both for the height parameter (FIG. 18) and for the aerial and root weight parameter (FIGS. 19 and 20).

Example 10

Comparison of In Vitro and In Vivo Nematicidal Activity of *Pseudomonas grimontii* Strain B949 Against *Meloydogine Javanica*.
Materials and Methods
Assay on Eggs:

The in vitro nematicidal ability of bacterium *P. grimontii* strain MR B949 on *M. javanica* eggs was evaluated in hatching chambers (Nunclon® Surface multiwell plates, Nunc, Denmark) in which 2 g of previously sterilized soil had been added. The substrate was then inoculated with an aqueous suspension containing 350 *M. javanica* eggs. *P. grimontii* strain MR B949 was applied at $1 \times 10^8$ CFU/mL. The hatching chamber was incubated at 26° C. for 3 weeks and periodic readings were taken 24 hours after applying the biological control agent and 1, 2 and 3 weeks later to determine the hatching percentage. Eight repetitions of each treatment, a negative control with a reference chemical at the commercially recommended dose (0.0125% Nemacur®; active ingredient: 25 fenamiphos) and a control with sterile distilled water to establish a reference for the results to the normal hatching percentage were included.

Assay on Juveniles:

The nematicidal ability of bacterium *P. grimontii* strain MR B949 was evaluated in vitro against *M. javanica* juvenile in hatching chambers (Nunclon® Surface multiwell plates, Nunc, Denmark), in which 2 g of previously sterilized soil were added. An aqueous suspension containing 200 juvenile forms of *M. javanica* was then added, and the biological control agent, *P. grimontii* strain MR B949, was applied at $1 \times 10^{10}$ CFU/mL. The hatching chamber was incubated at 26° C. for 7 days and counts were performed by means of the Hawksley® chamber after 24 hours (1 day) and after 7 days to determine the number of live juveniles (% mortality). A control with sterile distilled water and another control with a reference chemical (Nemacur® 0.0125%: active ingredient=fenamiphos) were included. Eight repetitions of each treatment were performed.

Assay In Vivo:

The in vivo nematicidal ability of bacterium *Pseudomonas grimontii* strain B949 was evaluated in the "Marmande" tomato variety against *M. javanica* juveniles. Each treatment consisted of 12 repetitions and each one was inoculated with 1,000 juveniles.

The assay schedule is as follows:

TABLE 14

*Pseudomonas grimantii* strain B949 application plan in an in vivo assay against *M. javanica*.

| Day 0 | Day 3 | Day 4 | Day 11 | Day 21 |
|---|---|---|---|---|
| Preventive treatment | Transplant | Nematode inoculation | $1^{st}$ treatment | $2^{nd}$ treatment |

The plants were placed in 1,000 cm$^3$ pots and treated with 10 mL of an aqueous solution containing *P. grimontii* strain B949 in the preventive treatment and with 15 mL in the 1st and $2^{nd}$ applications after transplant. The microorganism concentrations used for treatment were:

TABLE 15

Concentration of the aqueous solution containing *P. grimontii* strain B949 in each application.

| Treatment | Type | Doses | | |
|---|---|---|---|---|
| | | $1^{st}$ Application | $2^{nd}$ Application | $3^{rd}$ Application |
| Control | Sterile destilled water | H$_2$O | H$_2$O | H$_2$O |
| Nemacur | Reference formulation | 1% | 1% | 1% |
| B949 | IAGT | 1.32E+08 | 2.09E+08 | 1.71E+08 |

The reference chemical was 1% Nemacur® (fenamiphos). A control with sterile distilled water was also included.
The assay lasted for 2 months. After said time, the different parameters were evaluated to verify nematicidal activity of the microorganism:
  Reproduction: No. eggs/g root
  Fertility: No. eggs/mass
  Infectiveness: No. masses/plant
The evaluation of the last 2 parameters also helps to determine the effects of the microorganism in the pathogen life cycle (effects on adults nematodes).
Results and Discussion
Assay on Eggs

TABLE 16

Efficacy (%) corrected with respect to the control of the chemical used as a reference and *P. grimontii* strain MR B949 against *M. javanica* eggs.

| Treatments | Efficacy (%) |
|---|---|
| Fenamiphos | 63.60 |
| B949 | 0 |

Figure 21:
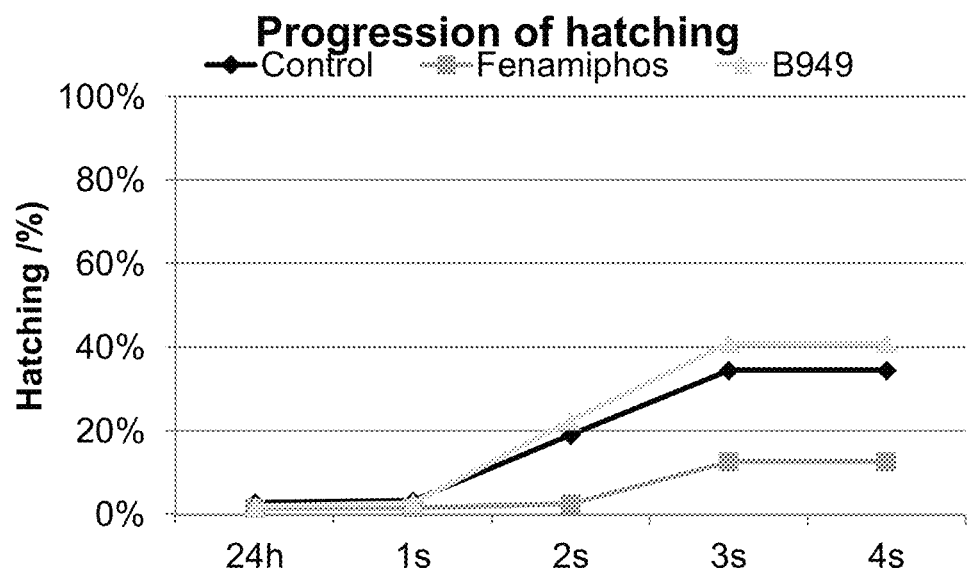
FIG. 21.—Progression of *M. javanica* egg hatching in the control and in treatments with the reference chemical(fenamiphos) and with *P. grimontii* strain B949 at different readings (days).
Figure 22:
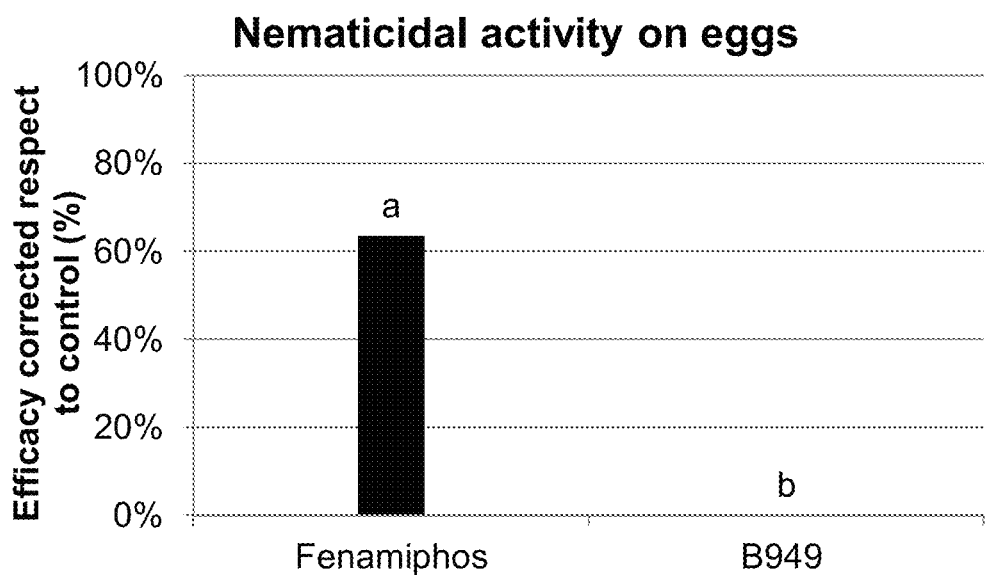
FIG. 22.—Nematicidal activity on *M. javanica* eggs of *P. grimontii* strain B949 and the reference chemical (fenamiphos) corrected with respect to the control. The different letters indicate statistically significant differences.

In the follow-up for the hatching of *M. javanica* eggs for the 21 days the assay lasted, treatment with *P. grimontii* strain MR B949 not showed reduction respect to the control (FIG. 21). Three weeks after applying the different treatments, 100% of the untreated eggs (control) and 100% of the eggs treated with *P. grimontii* strain MR B949 had hatched, whereas only 36.4% of eggs treated with Nemacur® (reference chemical) had hatched. Therefore, *P. grimontii* strain MR B949 had 0% efficacy in reducing hatching with respect to the control under in vitro conditions, whereas in the reference chemical, efficacy in reducing hatching was 63.60% (Table 16) (FIG. 22).

Assay on Juveniles

TABLE 17

Efficacy (%) corrected with respect to the control of the chemical used as a reference and *P. grimontii* strain MR B949 against *M. javanica* juveniles.

| Treatments | Efficacy (%) |
|---|---|
| Fenamiphos | 80.80 |
| B949 | 98.20 |

Figure 23:
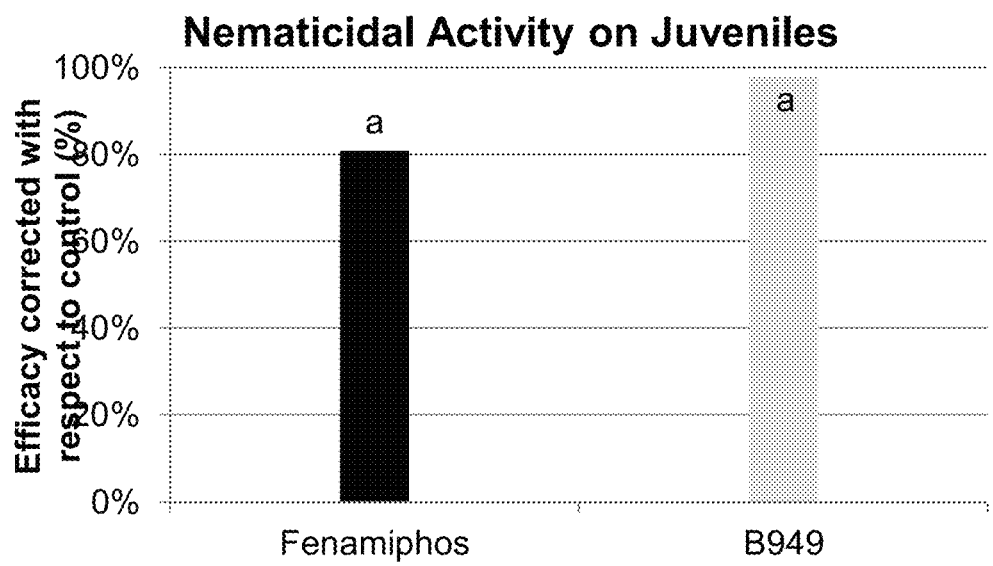
FIG. 23.—Nematicidal activity on *M. javanica* juveniles (J2) of *P. grimontii* strain B949 and the reference chemical (fenamiphos). The different letters indicate statistically significant differences.

*P. grimontii* strain MR B949 shows juvenile mortality percentages corrected with respect to the control in the order of 98.2% 7 days after application (Table 17). There are no significant differences with respect to the reference chemical used (FIG. 23).
Assay In Vivo

TABLE 18

Results of nematicidal efficacy of *P. grimontii* B949 and chemical reference corrected with respect to the control.

| Treatments | Efficacy corrected to the control (%) |
|---|---|
| Fenamiphos | 86.43 |
| B949 | 10.76 |

Figure 24:
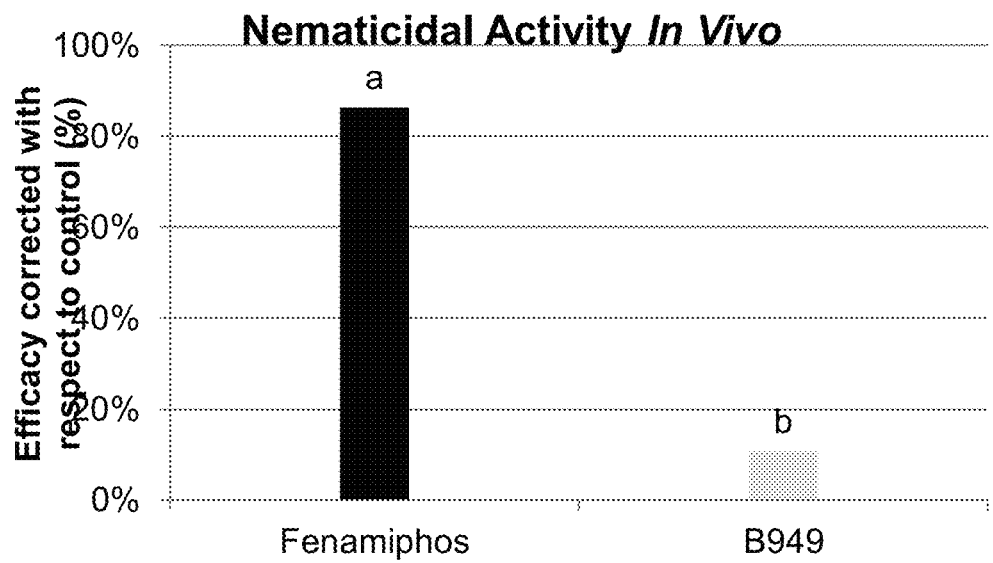
FIG. 24.—Nematicidal efficacy of *P. grimontii* strain B949 and the reference chemical (fenamiphos) on *M. javanica* eggs and juveniles in tomato plants.
Figure 25:
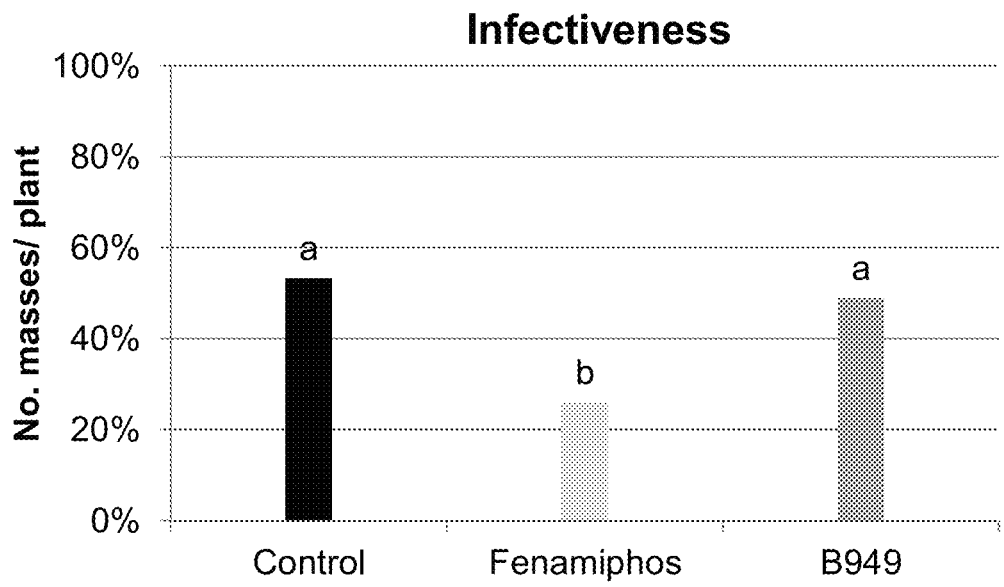
FIG. 25.—Infectiveness of the *M. javanica* adults treated with *P. grimontii* strain B949 and with the reference chemical (fenamiphos) compared with infectiveness of the control. The different letters indicate statistically significant differences.
Figure 26:
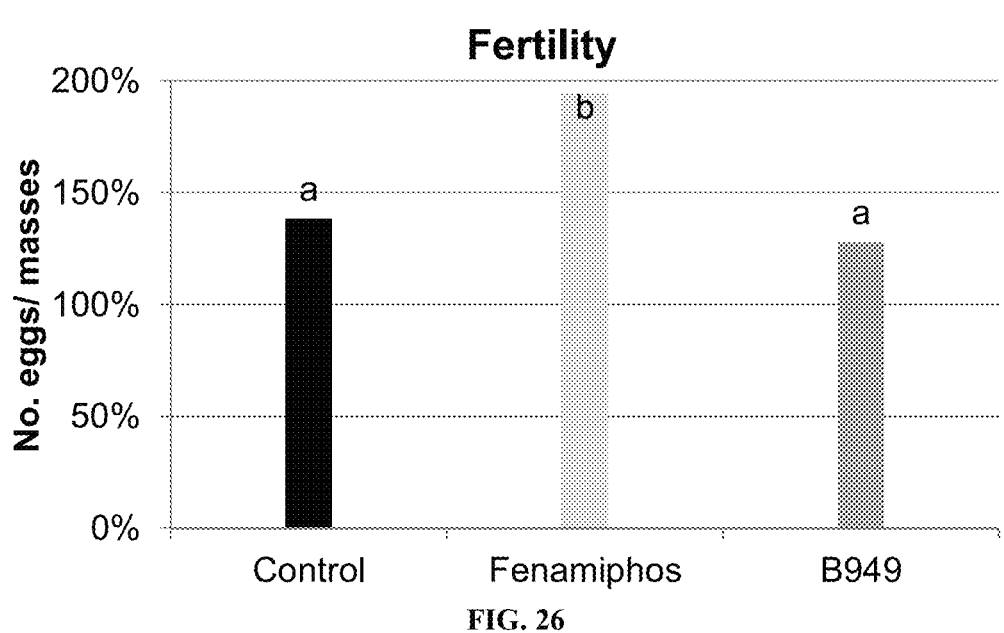
FIG. 26.—Fertility of *M. javanica* females treated with *P. grimontii* strain B949 and the reference chemical(fenamiphos) compared with the control. The different letters indicate statistically significant differences.

The results obtained in this assay showed that *P. grimontii* strain B949 had no nematicidal activity against *M. javanica* without statistically significant differences with control with nematodes. The chemical control used as a reference, obtained an efficacy of 86.43% (Table 18)(FIG. 24).
In addition, the fertility and infectiveness data, which are used to evaluate the activity of the microorganism in *M. javanica* adults, showed no statistically significant differences with control. *P. grimontii* strain B949 did not reduce the number of mass per plant and the number of eggs in each mass formed by adults females in the root. In conclusion, *P. grimontii* strain B949, does not reduce the ability of the parasite to cause infection (FIGS. 25 and 26).

Example 11

Comparison of In Vitro and In Vivo Nematicidal Activity of *Bacillus simplex* Strain B1169 Against *Meloydogine javanica*.
Materials and Methods
Assay on Eggs:
The in vitro nematicidal ability of bacterium *B. simplex* strain MR B1169 on *M. javanica* eggs was evaluated in hatching chambers (Nunclon® Surface multiwell plates, Nunc, Denmark) in which 2 g of previously sterilized soil had been added. The substrate was then inoculated with an aqueous suspension containing 350 *M. javanica* eggs. *B. simplex* strain B1169 was applied at 1×10$^8$ CFU/mL. The hatching chamber was incubated at 26° C. for 3 weeks and periodic readings were taken 24 hours after applying the biological control agent and 1, 2 and 3 weeks later to determine the hatching percentage. Eight repetitions of each treatment, a negative control with a reference chemical at the commercially recommended dose (0.0125% Nemacur®; active ingredient: fenamiphos) and a control with sterile distilled water to establish a reference for the results to the normal hatching percentage were included.

Assay on Juveniles:

The nematicidal ability of bacterium *B. simplex* strain B1169 was evaluated in vitro against *M. javanica* juvenile in hatching chambers (Nunclon® Surface multiwell plates, Nunc, Denmark), in which 2 g of previously sterilized soil were added. An aqueous suspension containing 200 juvenile forms of *M. javanica* was then added, and the biological control agent, *B. simplex* strain B1169, was applied at $1 \times 10^{10}$ CFU/mL. The hatching chamber was incubated at 26° C. for 7 days and counts were performed by means of the Hawksley® chamber after 24 hours (1 day) and after 7 days to determine the number of live juveniles (% mortality). A control with sterile distilled water and another control with a reference chemical (Nemacur® 0.01250: active ingredient=fenamiphos) were included. Eight repetitions of each treatment were performed.

Assay In Vivo

The in vivo nematicidal ability of bacterium *Bacillus simplex* strain B1169 was evaluated in the "Marmande" tomato variety against *M. javanica* juveniles. Each treatment consisted of 12 repetitions and each one was inoculated with 1,000 juveniles. The assay schedule was as follows:

TABLE 19

*Bacillus simplex* strain B1169 application plan in an in vivo assay against *M. javanica*.

| Day 0 | Day 3 | Day 4 | Day 11 | Day 21 |
|---|---|---|---|---|
| Preventive treatment | Transplant | Nematode inoculation | $1^{st}$ treatment | $2^{nd}$ treatment |

The plants were placed in 1,000 cm³ pots and treated with 10 mL of an aqueous solution containing *B. simplex* strain B1169 in the preventive treatment and with 15 mL in the 1st and $2^{nd}$ applications after transplant. The microorganism concentrations used for treatment were:

TABLE 20

Concentration of the aqueous solution containing *B. simplex* strain B1169 in each application.

| Treatment | Type | Doses | | |
|---|---|---|---|---|
| | | $1^{st}$ Application | $2^{nd}$ Application | $3^{rd}$ Application |
| Control | Sterile destilled water | H₂O | H₂O | H₂O |
| Nemacur | Reference formulation | 1% | 1% | 1% |
| B1169 | IAGT | 7.60E+07 | 7.40E+07 | 7.90E+07 |

The reference chemical was 1% Nemacur® (fenamiphos). A control with sterile distilled water was also included.

The assay lasted for 2 months. After said time, the different parameters were evaluated to verify nematicidal activity of the microorganism:

Reproduction: No. eggs/g root

Fertility: No. eggs/mass

Infectiveness: No. masses/plant

Results and Discussion

Assay on Eggs

TABLE 21

Efficacy (%) corrected with respect to the control of the chemical used as a reference and *B. simplex* strain MR B1169 against *M. javanica* eggs.

| Treatments | Efficacy (%) |
|---|---|
| Fenamiphos | 63.60 |
| B1169 | 0 |

Figure 27:
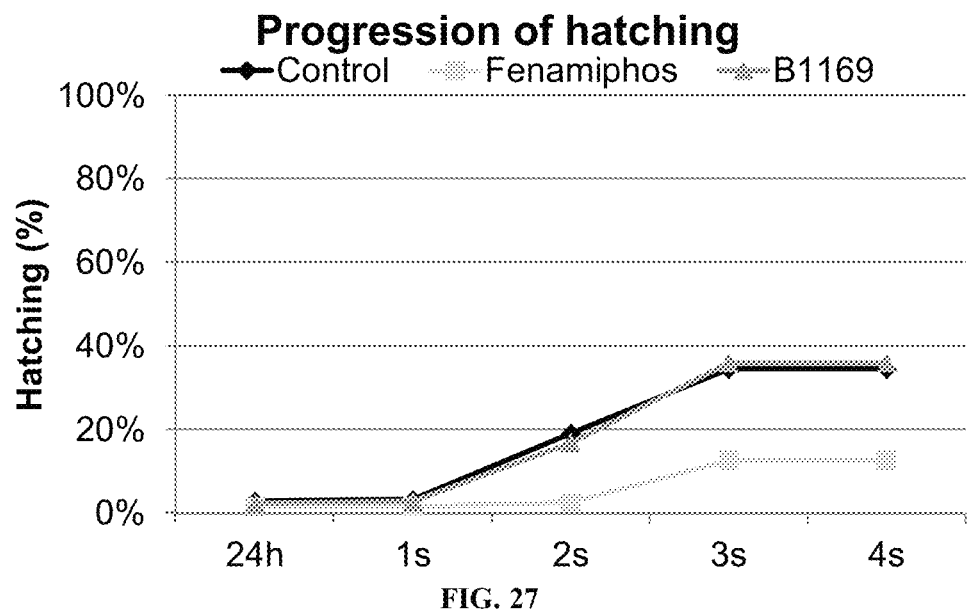
FIG. 27.—Progression of *M. javanica* egg hatching in the control and in treatments with the reference chemical(fenamiphos) and with *B. simplex* strain B1169 at different readings (days).
Figure 28:
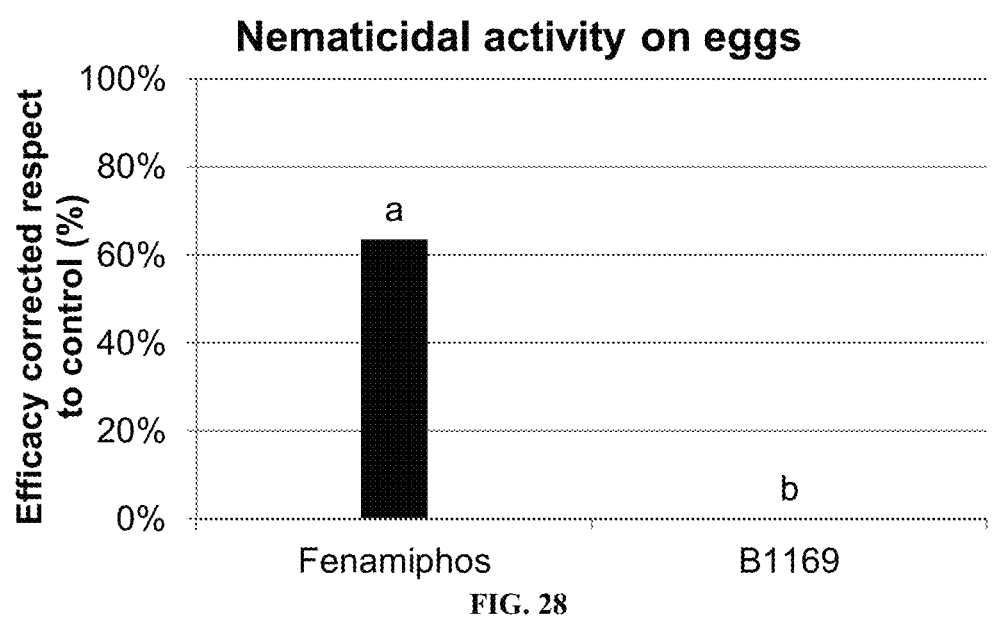
FIG. 28.—Nematicidal activity on *M. javanica* eggs of *B. simplex* strain B1169 and the reference chemical (fenamiphos) corrected with respect to the control. The different letters indicate statistically significant differences.

In the follow-up for the hatching of *M. javanica* eggs for the 21 days the assay lasted, treatment with *B. simplex* strain B1169 did not show a reduction with respect to the control (FIG. 27). Three weeks after applying the different treatments, 100% of the untreated eggs (control) and 100% of the eggs treated with *B. simplex* strain MR B1169 had hatched, whereas only 36.40% of eggs treated with Nemacur® (reference chemical) had hatched. Therefore, *B. simplex* strain B1169 had 0% efficacy in reducing hatching with respect to the control under in vitro conditions, whereas in the reference chemical, efficacy in reducing hatching was 63.60% (Table 21)(FIG. 28).

Assay on Juveniles

TABLE 22

Efficacy (%) corrected with respect to the control of the chemical used as a reference and *B. simplex* strain B1169 against *M. javanica* juveniles.

| Treatments | Efficacy (%) |
|---|---|
| Fenamiphos | 80.80 |
| B1169 | 76.90 |

Figure 29:
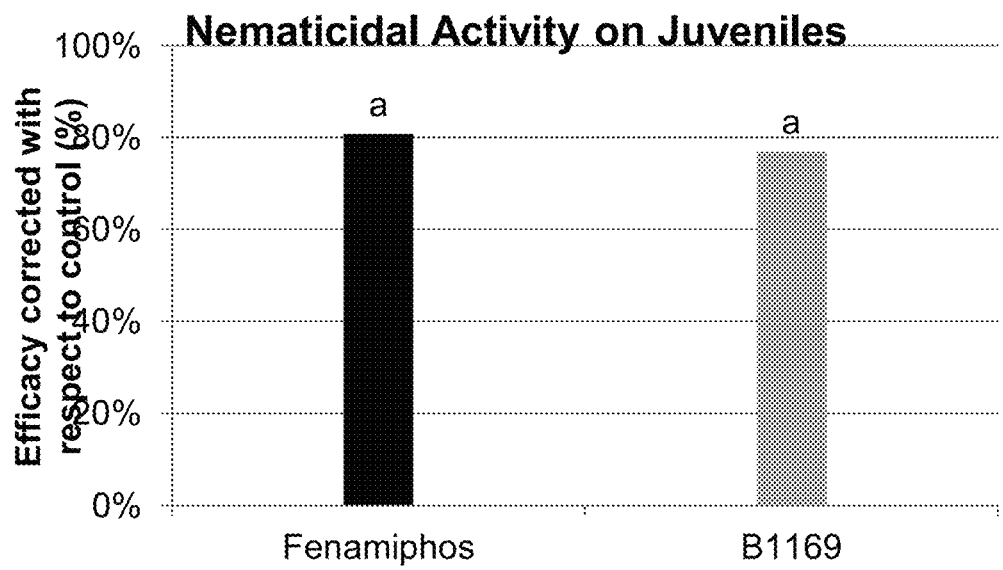
FIG. 29.—Nematicidal activity on *M. javanica* juveniles (J2) of *B. simplex* strain B1169 and the reference chemical (fenamiphos). The different letters indicate statistically significant differences.

*B. simplex* strain B1169 showed juvenile mortality percentages corrected with respect to the control in the order of 76.80% 7 days after application (Table 22). There were no significant differences with respect to the reference chemical used (FIG. 29).

Assay In Vivo

TABLE 23

Results of nematicidal efficacy of *B. simplex* strain B1169 and chemical reference corrected with respect to the control

| Treatments | Efficacy corrected to the control (%) |
|---|---|
| Fenamiphos | 86.43 |
| B1169 | 17.85 |

Figure 30:
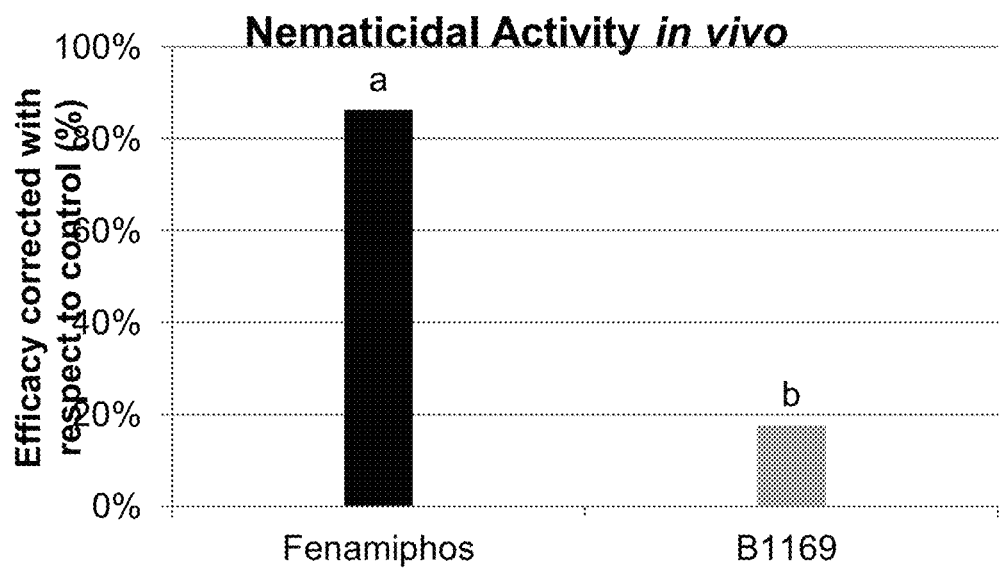
FIG. 30.—Nematicidal efficacy of *B. simplex* strain B1169 and the reference chemical (fenamiphos) on *M. javanica* eggs and juveniles in tomato plants.

The results obtained in this assay showed that *B. simplex* strain B1169 had no nematicidal activity against *M. javanica* without statistically significant differences respect to control with nematodes. The chemical control used as a reference, obtained an efficacy of 86.43% (Table 23)(FIG. 30).

Figure 31:
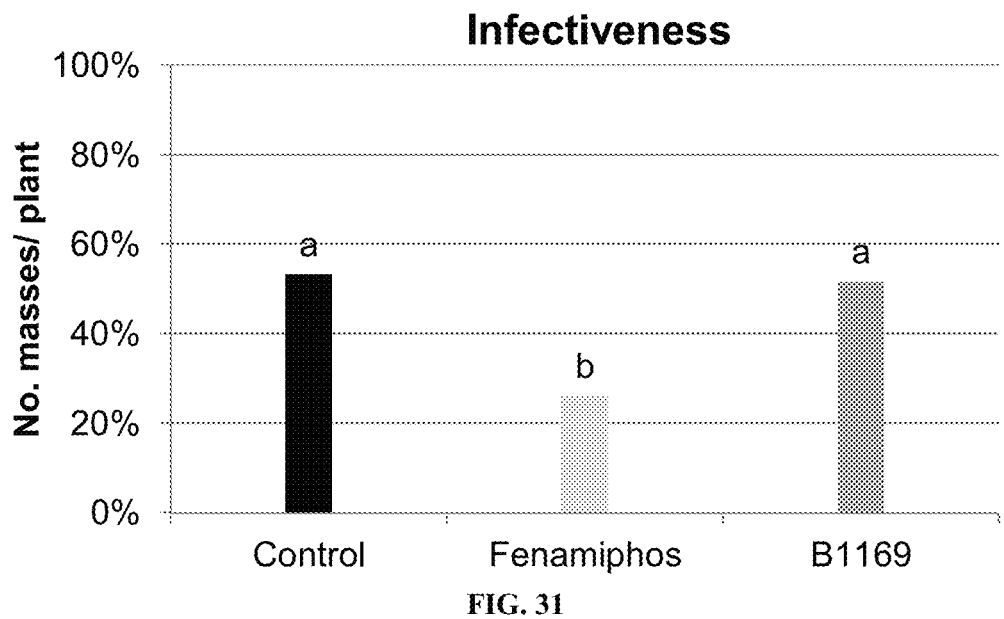
FIG. 31.—Infectiveness of the *M. javanica* adults treated with *B. simplex* strain B1169 and with the reference chemical (fenamiphos) compared with infectiveness of the control. The different letters indicate statistically significant differences.
Figure 32:
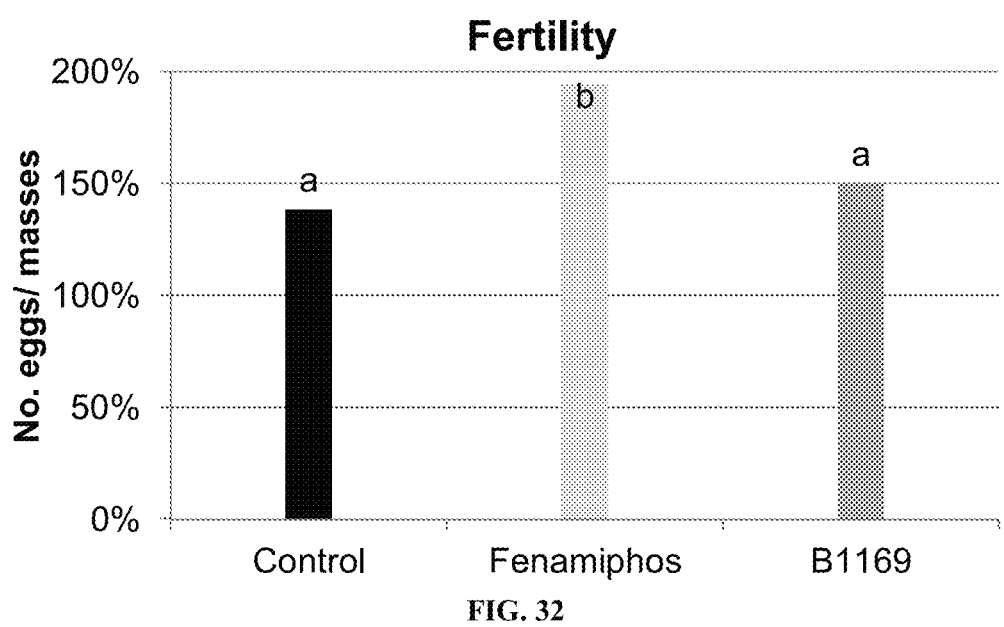
FIG. 32.—Fertility of *M. javanica* females treated with *B. simplex* strain B1169 and the reference chemical(fenamiphos) compared with the control. The different letters indicate statistically significant differences.

In addition, the fertility and infectiveness data, which were used to evaluate the activity of the microorganism in *M. javanica* adults, showed no statistically significant differences with control. *Bacillus simplex* strain B1169 did not reduce the number of mass per plant and the number of eggs in each mass formed by adults females in the root. In conclusion, *B. simplex* strain B1169, did not reduce the ability of the parasite to cause infection (FIGS. 31 and 32).

In conclusion, the existence of nematicide activity in an in vitro assay cannot be extrapolated to the existence of nematicide activity in vivo, where there are many factors involved in the process of biocontrol. Examples 10 and 11 also show that it is easier to reduce the nematode population of an organism when they are in the juvenile stage that when they are in the egg stage, which has more resistance given its characteristics.

Example 12

Comparison of In Vivo Growth-Promoting Activity of *Lysobacter enzymogenes* Strain MR B25 and B322 in Tomato Plants Materials and Methods To compare growth-promoting ability to *Lysobacter enzymogenes* MR B25 and *Lysobacter enzymogenes* B322, 25 tomato seeds from the "Marmande" variety were planted in trays with cells having a 20 mL capacity, with depleted substrate (peat at 10% and vermiculite: perlite (3:1)). They were deposited in a climatic chamber under controlled light, temperature and moisture conditions until completing the cotyledon stage, at which time technical grade active ingredient of *L. enzymogenes* MR B25 and B322 was applied at a concentration of $4 \times 10^7$ CFU/mL in a total volume of 5 mL/cell (=seed). Absolute control of sterile distilled water was also included. The assay lasted for 2 months. After this time period, the plants of the treatment and control were processed to evaluate the following parameters:
Height
Aerial fresh weight
Root fresh weight
Aerial dry weight
Root dry weight
Plant fresh weight
Plant dry weight Results and Discussion

TABLE 24

Results of plant growth promoting parameters and statistical analysis. Different letters are significant statistical difference.

| | Height | Aerial Fresh Weight | Root Fresh Weight | Aerial Dry Weight | Root Dry Weight | Plant Fresh Weight | Plant Dry Weight |
|---|---|---|---|---|---|---|---|
| Control | 5, 43 | 127, 00 | 67, 61 | 17, 35 | 5, 78 | 194, 61 | 23, 13 |
| B322 | 5, 73 | 135, 83 | 72, 04 | 19, 29 | 6, 21 | 207, 88 | 25, 50 |

TABLE 24-continued

Results of plant growth promoting parameters and statistical analysis. Different letters are significant statistical difference.

| | Height | Aerial Fresh Weight | Root Fresh Weight | Aerial Dry Weight | Root Dry Weight | Plant Fresh Weight | Plant Dry Weight |
|---|---|---|---|---|---|---|---|
| B25 | 7, 73 | 470, 77 | 201, 50 | 47, 31 | 13, 74 | 672, 27 | 61, 05 |
| P val | <0, 001 | <0, 001 | <0, 001 | <0, 001 | <0, 001 | <0, 001 | <0, 001 |

LSD test

| | | | | | | | |
|---|---|---|---|---|---|---|---|
| Control | a | a | a | a | a | a | a |
| B322 | a | a | a | a | a | a | a |
| B25 | b | b | b | b | b | b | b |

Figure 33:
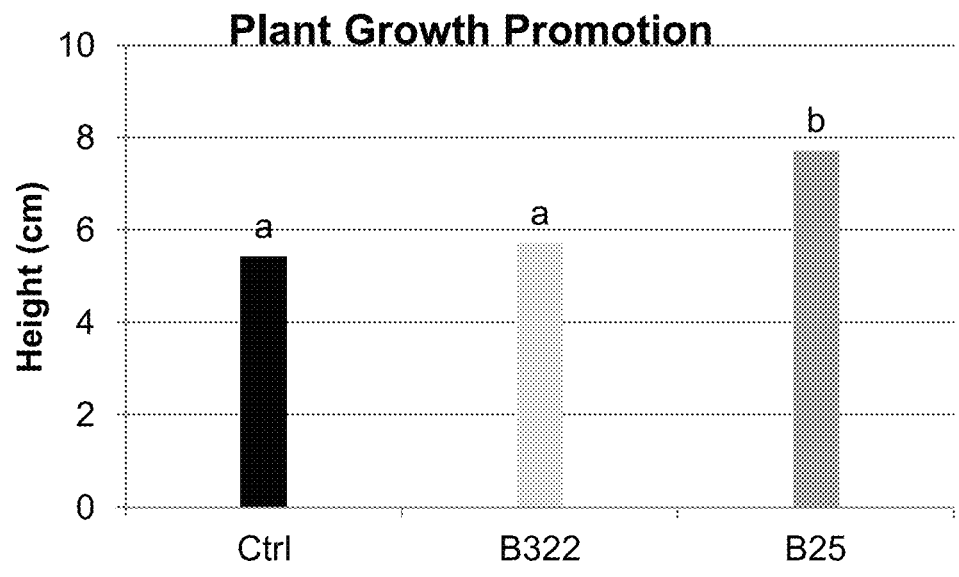
FIG. 33.—Comparison of stem height in plants treated with *L.enzymogenes* MR B25 and B322 compared with the control. The different letters indicate statistically significant differences.
Figure 34:
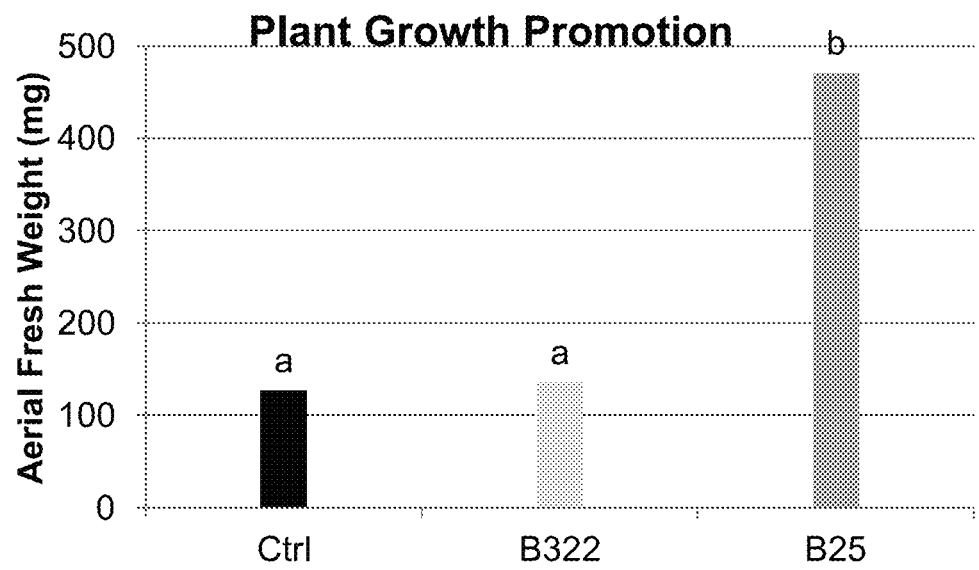
FIG. 34.—Aerial fresh weight of the plant treated with *L. enzymogenes* strain MR B25 compared with *L. enzymogenes* strain B322 and the control used. The different letters indicates statistically significant difference.
Figure 35:
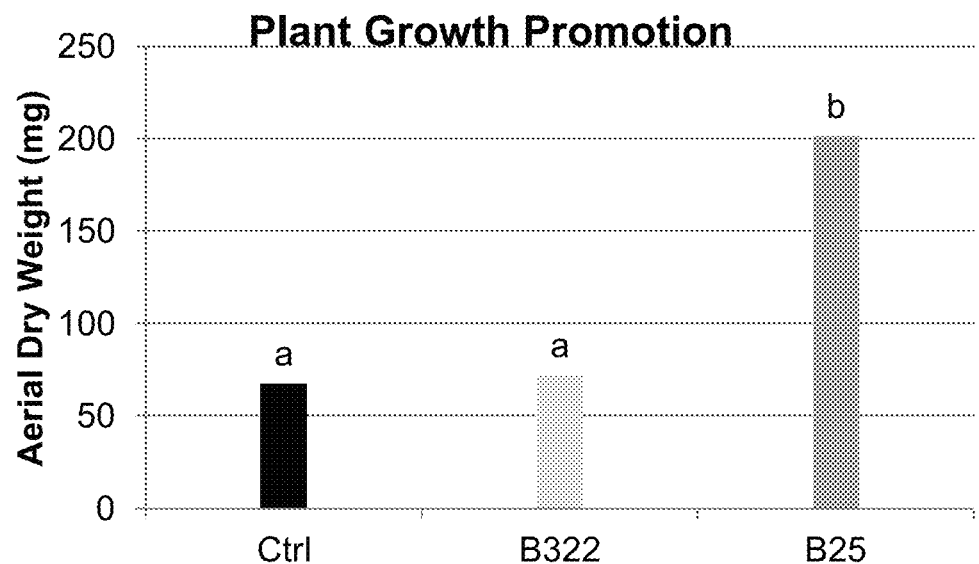
FIG. 35.—Aerial dry weight of the plant treated with *L. enzymogenes* strain MR B25 compared with *L. enzymogenes* strain B322 and the control used. The different letters indicates statistically significant difference.
Figure 36:
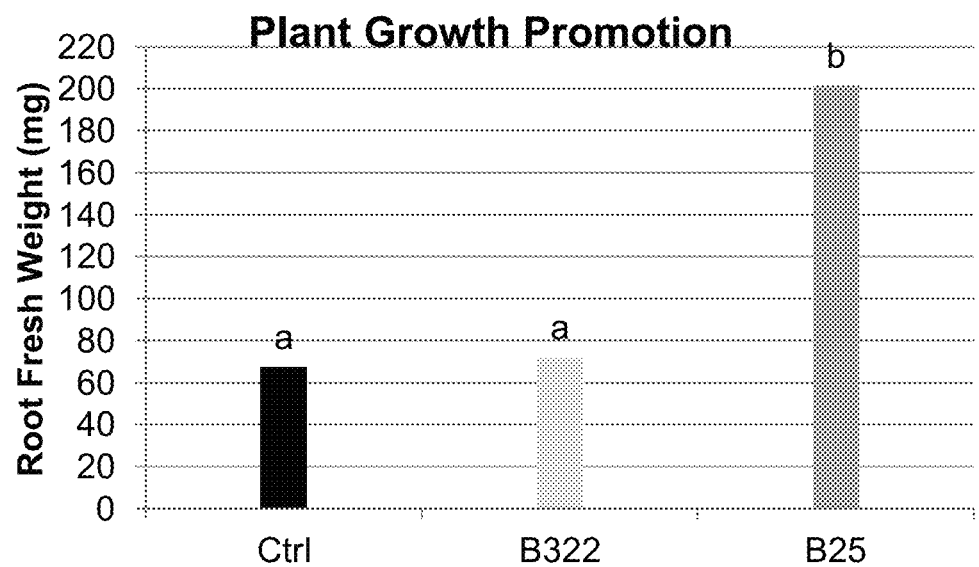
FIG. 36.—Root fresh weight of the plant treated with *L. enzymogenes* strain MR B25 compared with *L. enzymogenes* strain B322 and the control used. The different letters indicates statistically significant difference.
Figure 37:
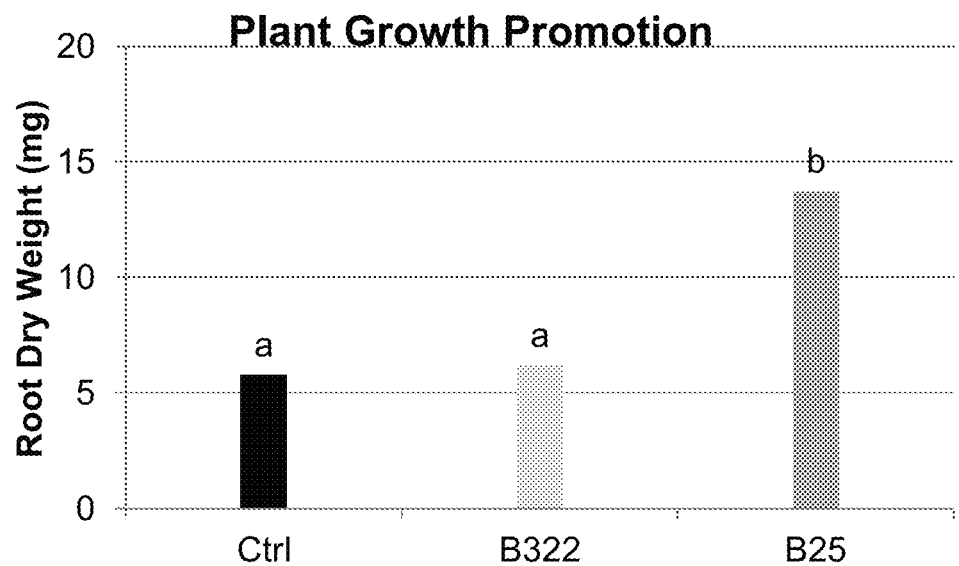
FIG. 37.—Root dry weight of the plant treated with *L. enzymogenes* strain MR B25 compared with *L. enzymogenes* strain B322 and the control used. The different letters indicates statistically significant difference.

*L. enzymogenes* strain MR B25 promoted plant growth with statistically significant differences with respect to the control and the treatment with *L. enzymogenes* strain B322 both for the height (FIG. 33) and aerial and root weight parameters (FIGS. 34, 35, 36 and 37). *L. enzymogenes* B322 showed no promoting growth for any parameter evaluated, without statistically significant difference with control (table 24).

TABLE 25

Promoting growth activity based on dry weight of the plant respect to the control.

| Treatments | Promoting Growth Activity (fold) |
|---|---|
| B322 | 0.10 |
| B25 | 1.64 |

Figure 38:
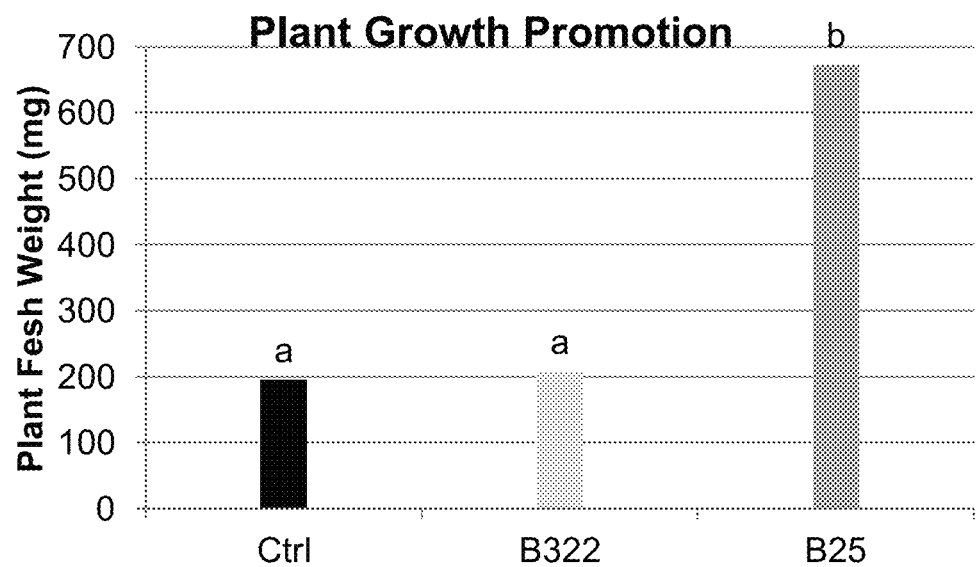
FIG. 38.—Plant fresh weight of the plant treated with *L. enzymogenes* strain MR B25 compared with *L. enzymogenes* strain B322 and the control used. The different letters indicates statistically significant difference.
Figure 39:
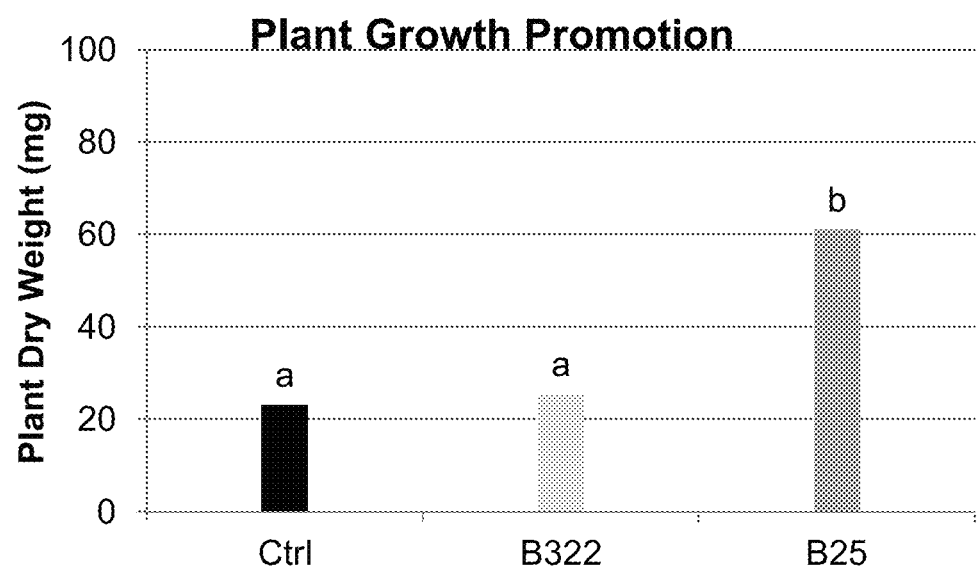
FIG. 39.—Plant dry weight of the plant treated with *L. enzymogenes* strain MR B25 compared with *L. enzymogenes* strain B322 and the control used. The different letters indicates statistically significant difference.

The results of this study concluded that *L. enzymogenes* strain MR B25 promotes plant growth without the need of pathogen presence (FIGS. 38 and 39). Other studies presented earlier, demonstrated that this microorganism is able to help to the growth development with and without pathogen. This characteristic is not specie specific but it is a strain property.

DEPOSIT OF BIOLOGICAL MATERIAL

*Lysobacter enzymogenes* strain MR B25 has been deposited in the Spanish Type Culture Collection (CECT) (Edificio 3 CUE, Universidad de Valencia, Parc Cientific Universitat de València, Catedrático Agustin Escardino, 9; 46980 Paterna, Valencia) under the conditions set forth in the Budapest Treaty. The deposit took place on Mar. 7, 2014 and the number assigned to said deposit was CECT 8565.

The invention claimed is:

1. A microorganism from the species *Lysobacter enzymogenes*, identified as *L. enzymogenes* strain MR B25, deposited in the Spanish Type Culture Collection (CECT) with accession number CECT 8565, having nematicidal activity and/or the ability to promote plant growth in the absence of nematodes, wherein the microorganism is mixed with an agriculturally acceptable excipient.

2. The microorganism according to claim 1, wherein said microorganism has nematicidal activity on a nematode from the species *Meloidogyne javanica*.

3. The microorganism according to claim 1, wherein said microorganism has the ability to promote plant growth in a plant from the family Solanaceae.

4. A method for biologically controlling a nematode comprising applying to said nematode the mixture of claim 1.

5. A method for preventing plant infection caused by a nematode comprising applying an effective amount of the mixture of claim 1 on said plant, on the seed of said plant, in the soil surrounding said plant or on a nematode susceptible of infecting said plant, or alternatively planting a seed of said plant supplemented with the mixture of claim 1.

6. A method for treating a plant infected by a nematode comprising applying an effective amount of the mixture of claim 1 on said plant or in the soil surrounding said plant.

7. A method for stimulating plant growth comprising applying an effective amount of the mixture of claim 1 on said plant, on the seed of said plant or in the soil surrounding said plant, or alternatively planting a seed of said plant supplemented with the mixture of claim 1.

8. The method according to claim 5, wherein the plant belongs to the family Solanaceae.

9. The method according to claim 7, wherein the plant belongs to the family Solanaceae.

10. The method according to claim 5, wherein the effective amount of the mixture of claim 1 is applied in a first application before transplanting the plant, in a second application after transplanting the plant, and at least a number "n" of applications, wherein "n" is an integer comprised between 1 and 10, wherein each of said "n" applications is applied between 10 and 20 days after the preceding application.

11. The method according to claim 6, wherein the effective amount of the mixture of claim 1 is applied in a first application before transplanting the plant, in a second application after transplanting the plant, and at least a number "n" of applications, wherein "n" is an integer comprised between 1 and 10, wherein each of said "n" applications is applied between 10 and 20 days after the preceding application.

12. The method according to claim 7, wherein the effective amount of the mixture of claim 1 is applied in a first application before transplanting the plant, in a second application after transplanting the plant, and at least a number "n" of applications, wherein "n" is an integer comprised between 1 and 10, wherein each of said "n" applications is applied between 10 and 20 days after the preceding application.

* * * * *